United States Patent
Goel

(10) Patent No.: US 7,777,071 B2
(45) Date of Patent: Aug. 17, 2010

(54) PRODUCTION OF CARNITINE CONJUGATE INTERMEDIATES

(75) Inventor: Om P Goel, Ann Arbor, MI (US)

(73) Assignee: SSV Therapeutics, Inc., Ann Arbor, MI (US)

( * ) Notice: Subject to any disclaimer, the term of this patent is extended or adjusted under 35 U.S.C. 154(b) by 477 days.

(21) Appl. No.: 11/660,299

(22) PCT Filed: Aug. 11, 2006

(86) PCT No.: PCT/US2006/031362

§ 371 (c)(1),
(2), (4) Date: Feb. 14, 2007

(87) PCT Pub. No.: WO2008/018877

PCT Pub. Date: Feb. 14, 2008

(65) Prior Publication Data

US 2009/0012160 A1 Jan. 8, 2009

Related U.S. Application Data

(63) Continuation-in-part of application No. 10/987,839, filed on Nov. 12, 2004, now Pat. No. 7,345,190.

(51) Int. Cl.
*C07C 69/74* (2006.01)
(52) U.S. Cl. ..................... 560/127; 514/547
(58) Field of Classification Search ............... 560/127; 514/547
See application file for complete search history.

(56) References Cited

U.S. PATENT DOCUMENTS

| | | | |
|---|---|---|---|
| 4,255,449 A | 3/1981 | Carazza | |
| 4,315,944 A | 2/1982 | Ramacci et al. | |
| 4,689,344 A | 8/1987 | Bar-Tana | |
| 4,963,525 A | 10/1990 | Alexander et al. | |
| 5,008,288 A | 4/1991 | Stracher et al. | |
| 5,756,544 A | 5/1998 | Bisgaier et al. | |
| 6,180,667 B1 | 1/2001 | Foresta et al. | |
| 6,232,346 B1 | 5/2001 | Sole et al. | |
| 6,790,953 B2 | 9/2004 | Dasseux et al. | |
| 2001/0011081 A1 | 8/2001 | Cavazza | |
| 2003/0114460 A1 | 6/2003 | Hughes et al. | |
| 2005/0101572 A1* | 5/2005 | Goel | 514/114 |
| 2006/0041017 A1 | 2/2006 | Chopra | |

FOREIGN PATENT DOCUMENTS

WO  WO/99/00116 A2  1/1999

OTHER PUBLICATIONS

Frenkel, B. et al., Biochem. J. 298, 409-414 (1994).
Cramer, Clay T. et al., J. Lipid Res. 45, 1289-1301 (2004).
Lango, T. et al., Cardiovascular Res. 51, 21-29 (2001).
Fritz, Irving B. et al., TiPS 14, 355-360 (Oct. 1993).
Criddle, D. N. et al., Br. J. Pharmacology 99, 477-480 (1990).
Alexander et al. 1987, CAS:107:223274.
Gaskell et al., 1986, CAS:105:168289.
Yamamoto et al., 1988, CAS:109:51106.
Yamaguchi et al., 1989, CAS:111:75896.
Huang et al., 1992, CAS:116:18011.
Pourforzam et al., 1993, CAS:119:91967.
Nakanishi et al., 1994, CAS:120:245706.
Montgomery et al., 1989, CAS:110:169579.
Millington et al., 1989, CAS:111:190899.

* cited by examiner

*Primary Examiner*—Kamal A Saeed
*Assistant Examiner*—Valerie Rodriguez-Garcia
(74) *Attorney, Agent, or Firm*—Technology Law PLLC; Karen L. Kimble

(57) ABSTRACT

The present invention discloses novel dual prodrug compounds of formula (1), methods for their preparation and intermediates in their syntheses, formula (1): wherein A is a single bond, —O—, or —CH$_2$—; m and n vary independently and are an integer from 1 to 15; p and q vary from 0 to an integer from 1 to 4; B is a single bond or —CR$^3$R$^4$; D is formula (2): or formula (3): and X is halogen; R$^1$ to R$^4$ are various substituents selected to optimize the physiochemical and biological properties such as, lipophilicity, bioavailability, and pharmacokinetics of compounds of Formula 1; and R$^1$ and R$^2$ or R$^3$ and R$^4$ may optionally be tethered together to form a 3- to 7-membered alicyclic ring. These compounds are useful for the treatment of various infections, metabolic, cardiovascular and neurological disorders.

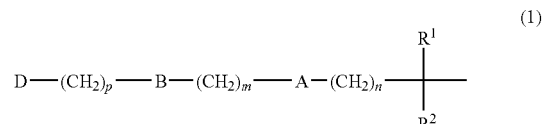

(1)

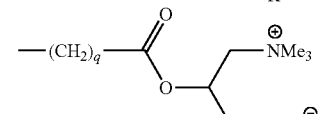

(2)

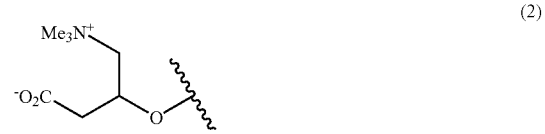

(3)

1 Claim, No Drawings

PRODUCTION OF CARNITINE CONJUGATE INTERMEDIATES

FIELD OF THE INVENTION

This present invention relates to novel carnitine ester and ether conjugates of hypolipidemic agents and pharmaceutically acceptable salts thereof, and methods of producing them. The novel compositions of the present invention are useful for the treatment of cardiovascular diseases, metabolic diseases, obesity, diabetes, gastrointestinal disorders, inflammation, cancer, anemia, renal anemia, Alzheimer's disease, for modulating peroxisome proliferation by peroxisome proliferator-activated receptors (PPARs), and as antimicrobials, antivirals, and hair growth stimulants.

BACKGROUND OF THE INVENTION

Coronary heart disease (CHD) is a leading cause of lowering the quality of human life and mortality among the populations of the developed nations as well as the economically fast-growing countries, accompanied by worldwide rise in obesity, diabetes, including among young adults, due to high-calorie diets and poor exercise. The cardiovascular disease is characterized by clogged arteries and reduced supply of blood and nutrients to the heart muscle caused by lipid deposition inside the arterial wall. Hyperlipidemia or hyperlipoproteinemia (form of lipid-protein complexes) may be caused by genetic factors or by obesity and metabolic disorders. Lipid-protein complexes are spherical aggregates consisting of a hydrophobic core composed of lipids (triglycerides and cholesterol esters) surrounded by a hydrophilic exterior shell of about 2 nm composed of apoproteins, cholesterol, and phospholipids. The hydrophilic polar surface keeps the lipids dissolved and circulating in the plasma. Based on size and density, four main lipoproteins are prevalent in the plasma: chylomicrons, very low density lipoprotein (VLDL), low density lipoprotein (LDL or LDL-C), and high density lipoprotein (HDL or HDL-C). Chylomicrons and VLDL are rich in triglycerides and cholesterol. They are the sources of fatty acids in muscle and adipose tissues. LDL-C particles are rich in cholesterol and are produced in the liver from dietary cholesterol, from liver-synthesized cholesterol, and from remnants of chylomicrons and VLDL that have entered the extrahepatic tissues from the general circulation [see Ziegler, A. et al., *Color Atlas of Pharmacoloy*, 2$^{nd}$ Edition, pp. 154-157, Thieme Publishers, 2000].

High levels of LDL-C (referred to as 'bad cholesterol') is a well-established major risk factor in CHD, but can be effectively treated with HMG-CoA reductase inhibitors (statins) leading to substantial reduction in cardiovascular morbidity and mortality [see Scandinavian Simvastatin Study Group, *Lancet* 344, 1383-1389 (1994)]. HDL-C particles (referred to as 'good cholesterol') are responsible for a cleansing mechanism called 'reverse cholesterol transport', where the cholesterol is transported from extrahepatic tissues to the liver for catabolic destruction and excretion. It is widely accepted that low levels of IDL-C and high levels of triglycerides in plasma are important risk factors contributing to CHD. [see NCEP Panel, *Circulation* 89, 1329 (1994)].

Levocarnitine (L-carnitine or vitamin $B_T$) belongs to a class of water soluble vitamins which include vitamin $B_{12}$, folio acid, biotin, vitamin $B_6$, and mevalonic acid. It occurs naturally, and serves as a cofactor in fatty acid metabolism for energy production. This cofactor functions by binding activated fatty acids in the form of acyl carnitine (carnitine shuttle). Use of L-carnitine in the treatment of hyperlipoproteinemia, hyperlipidemia, and myocardial dysfunction has been the subject of intense investigation [see, for example, Carazza, C., U.S. Pat. No. 4,255,449; Ramacci, M., U.S. Pat. No. 4,315,944; Siliprandi, N., *Hypolipidemic Drugs*, G. Ricci (Ed.), New York: raven, 1982; Yamazaki, N., *Lipid* 1(2) (1990); Pauly D. F. et al., *Am. J. Kidney Dis.* 41, S35-S43 (2003); Calvani, M., et al., *Basic Res. Cardiol.* 95, 75-83 (2000)]. L-carnitine has also been reported to be useful as an adjuvant therapy in the management of renal anemia [Cianciaruso, B., et al., *Contrib. Nephrol,* 137, 426-430 (2002)]. Propionyl carnitine (the propionic ester of carnitine) has been shown to improve cardiac function [see, for example, Wiseman, L. R, et al., *Drugs Aging* 12, 243-248 (1998); Ferrari, R. et al., *Developments in Cardiovascular Medicine* 162, 323 (1995)]. Acetyl carnitine has been proposed as a possible therapeutic agent for Alzheimer's disease [Pettegrew, J. W., et al., *Expert Review of Neurotherpeutics* 2, 647-654 (2002)]. Recently, CPS 124, a carnitine monothiophosphate derivative which is a reversible and competitive inhibitor of carnitine palmitoyl transferase I, is reportedly undergoing clinical development for the treatment of non-insulin dependent diabetes mellitus (NIDDM) [Anderson, R. C., *Curr. Phawm. Des.* 4, 1-16 (1998)]. Nicotinyl carnitine derivatives have been studied as anticholesteremics and hypolipemics [Chibata, I., et al., U.S. Pat. No. 4,032,641].

In humans, fibrates such as clofibrate, bezafibrate, fenofibrate, etofibrate, gemfibrozil, and G10-2331, which are agonists of PPAR-alpha, have been successfully used to treat hypertriglyceridemia. They function by increasing the clearance and decreasing the synthesis of VLDL. The fibrates, however, have only a modest effect (10-20%) in increasing HDL-C levels [see, for example, Staels, B., et al., *Circulation* 98, 2088-2093 (1998); Harwood, H. J., et al., *Emerging Drugs* 3, 147 (1998)]. Clinical development of cardioprotective HDL-C elevating agents is a major therapeutic goal. Recently, it was shown that oxa-substituted α,ω-alkanedicarboxylic acids and related compounds raise serum HDL-levels significantly [see, for example, Bisagaier, C. L., et al., U.S. Pat. No. 5,756,544; Dasseux, J. L., et al., U.S. Pat. No. 6,646, 170]. In particular, CI-1027 has been in clinical trials. Also, long chain α,ω-alkanedicarboxylic acids are also in clinical development as hypolipidemic agents [see Bar-Tana, J. U.S. Pat. Nos. 4,689,344 and 4,711,8961].

The peroxisome proliferator activated receptor (PPARα) is one among a set of ligand-activated transcription factors in the nuclear receptor superfamily. Other distinct PPAR subtypes are $PPAR_\gamma$, $PPAR_\delta$, and $PPAR_\beta$, [see Mangelsdorf, D. J., et al., *Cell* 83, 841-850 (1995); Green, S., et al., *Mol. Cell. Endocrinol.* 100, 149-153 (1994); Dreyer, C., et al., *Cell* 68, 879-887 (1992); Kliewer, S. A., et al., *Recent Prog. Horm. Res.* 56, 239-263 (2001); Berger, J., et al., *Annu. Rev. Med.* 53, 409-435 (2002)]. In particular, $PPAR_\gamma$ has been shown to be the primary receptor involved in the antidiabetic activity of thiazolidinediones (TZDs) [see Tong, Q., et al., *Rev. Endocr. Metab. Disord.* 2, 349-355 (2001); Rosen, E. D., et al., *Genes Dev.* 14, 1293-1307 (2000)]. Current discovery efforts in metabolic diseases are focused on the design of balanced, dual $(PPAR)_{\alpha/\gamma}$ agonists to treat hyperlipidemia, type 2 diabetes (NIDDM) and obesity. Interestingly, many of the lead dual $(PPAR)_{\alpha/\gamma}$ agonists entering preclinical and clinical development contain the essential structural features of classical fibrates designed to block the β-oxidation pathway of fatty acids [see Xu, Y., et al., *J. Med. Chem.,* 47, 2422-2425 (2004); Koyama, H., et al., *J. Med. Chem.* 47, 3255-3263 (2004)].

The need to improve the action of known drugs and multiple drug delivery has been recognized, but the methods to accomplish this objective have not been clearly understood. Published U.S. Patent Application 2003/0114460 discloses the concept of pharmaceutical conjugates that have enhanced pharmacokinetics. Richard Morphy et al., *J. Med. Chem.* 48, 6523-6543 (2005), have reviewed the design of multiple conjugated ligands for improved drug delivery as a new emerging paradigm. Improvements for commercial success have tried to using this approach and are continuously still being sought.

U.S. Patent Application 2005/0101572, published May 12, 2005, discloses related compounds of Formula 1 of this invention for use as dual prodrugs. The disclosed processes for their preparation are described by two chemical schemes (1 and 2) which are of very limited scope, give low yields of product, and purification of the product is difficult. Thus the present processes and compounds of the present invention were sought.

SUMMARY OF THE INVENTION

The present invention discloses dual prodrug compositions of Formula 1, and methods of their production, including intermediates,

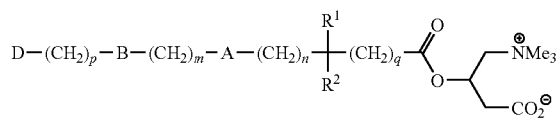

Formula 1 wherein: A is selected from the group consisting of a single bond, —O— or —CH$_2$—; m and n vary independently and are integers from 1 to 15; p and q vary independently from 0 to an integer from 1 to 4; B is a single bond, or —CR$^3$R$^4$; D is

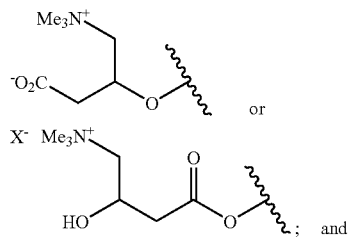

X is halogen;

R$^1$ to R$^4$ are various substituents selected to optimize the physiochemical and biological properties such as lipophilicity, bioavailability, and pharmacokinetics of compounds of Formula 1; and R$^1$ and R$^2$ or R$^3$ and R$^4$ may optionally be tethered together to form a 3- to 7-membered alicyclic ring.

These substituents for R$^1$ to R$^4$ include, but are not limited to, hydrogen, alkyl, alkenyl, alkynyl, cylcoalkyl, acyl, hydroxyl, hydroxyalkyl, aryl, amino, aminoalkyl, alkoxyl, aryloxyl, carboxyl, halogen, alkoxycarbonyl, trihaloalkyl, cyano, and other suitable electron donating or electron withdrawing groups.

Various novel intermediates have been used in the process to prepare these compounds of Formula 1 as described later in the specification.

DETAILED DESCRIPTION OF THE INVENTION

The present invention introduces a novel concept referred to as the 'double prodrug' approach which involves the preparation of novel covalent conjugates comprising two or more drugs, and their use in the treatment of various cardiovascular disorders. A suitable covalent attachment of two more of these cardiovascular agents may have a significant therapeutic value in that a single molecular entity may have multiple therapeutic effects resulting from diverse, but synergistic mechanisms of action, and controlled release of both drugs in vivo through enzymatic hydrolysis of the conjugate. The present invention is not limited to cardiovascular applications; other therapeutic applications, including CNS disorders, antimicrobials, antivirals, diabetes, cancer, inflammation, and the like are also contemplated. It is anticipated that novel fibrate type molecular entities entering clinical trials are also candidates for conjugation with L-carnitine for improved efficacy and intended therapeutic applications; and are claimed in this application under the concept of dual prodrugs.

The present invention provides novel dual prodrug compounds and the corresponding pharmaceutically acceptable salts thereof of Formula 1,

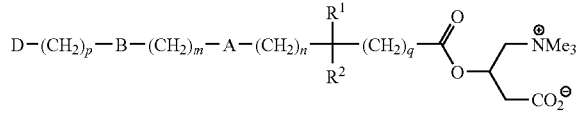

Formula 1 wherein: A is selected from the group consisting of a single bond, —O— or —CH$_2$—; m and n vary independently and are integers from 1 to 15; p and q vary independently from 0 to an integer from 1 to 4; B is a single bond or —CR$^3$R$^4$; D is

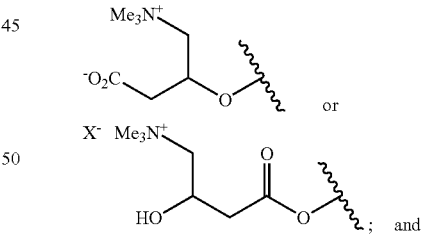

X is halogen;

R$^1$ to R$^4$ are independently selected from the group consisting of hydrogen; C$_1$-C$_6$ alkyl; C$_3$-C$_6$ cycloalkyl; C$_2$-C$_6$ alkenyl; C$_6$ alkynyl; C$_5$-C$_{10}$ aryl unsubstituted or substituted with C$_1$-C$_6$ alkyl, hydroxyl, C$_1$-C$_6$ alkoxyl, 1,3-dioxolanyl, cyano, halo, nitro, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, C$_1$-C$_6$ acylamino, mercapto, C$_1$-C$_6$ alkylthio, C$_1$-C$_6$ mercaptoalkyl, and C$_1$-C$_6$ alkoxycarbonyl; and C$_5$-C$_6$ arylalkyl unsubstituted or substituted with C$_1$-C$_6$ alkyl, hydroxyl, C$_1$-C$_6$ alkoxyl, 1,3-dioxolanyl, cyano, halo, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, mercapto, $C_1$-$C_6$ alkylthio, $C_1$-$C_6$ mercaptoalkyl, and $C_1$-$C_6$ alkoxycarbonyl; $C_1$-$C_6$ carboxyalkyl; $C_1$-$C_6$ acylamino; $C_1$-$C_6$ sulfonatoalkyl; $C_1$-$C_6$ sulfamylalkyl; and $C_1$-$C_6$ phosphonatoalkyl; and $R^1$ and $R^2$ or $R^3$ and $R^4$ may optionally be tethered together to form a 3- to 7-membered alicyclic ring.

A preferred embodiment of the present invention is represented by Formula 1, wherein: A is —O— or —CH$_2$—; m and n vary independently and are an integer from 1 to 6; p and q vary independently from 0 to an integer from 1 to 3; B is —CR$^3$R$^4$; D is

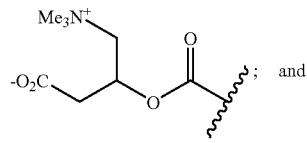

$R^1$ and $R^2$ are independently selected from the group consisting of hydrogen; $C_1$-$C_6$ alkyl, and $C_3$-$C_6$ cycloalkyl; and $R^1$ and $R^2$ or $R^3$ and $R^4$ may optionally be tethered together to form 3- to 7-membered alicyclic ring.

Another preferred embodiment of the present invention is represented by Formula 1, wherein: A is —O— or —CH$_2$—; m and n vary independently and are an integer from 1 to 6; p and q vary from 0 to an integer from 1 to 3; B is —CR$^3$R$^4$; D is

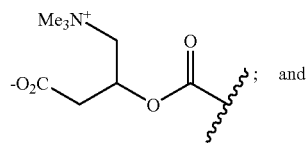

$R^1$ to $R^4$ are independently hydrogen or $C_1$-$C_6$ alkyl.

Another preferred embodiment of the present invention is represented by Formula 1, wherein: A is —O— or —CH$_2$—; m is 4; n is 4; p varies from 0 to 3; q is 0 or 1; B is —CR$^3$R$^4$; D is

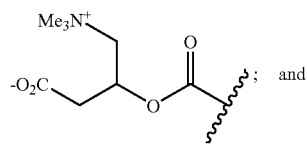

$R^1$ to $R^4$ are methyl groups.

A further preferred embodiment of the present invention is those compounds of Formula 1 wherein: A is —O— or —CH$_2$—; m and n vary independently and are an integer from 1 to 6; p and q vary independently from 0 to an integer from 1 to 3; B is —CR$^3$R$^4$; D is

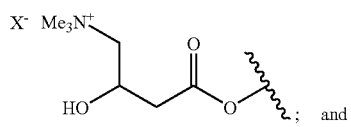

X is Cl or Br;

$R^1$ and $R^2$ are independently selected from the group consisting of hydrogen; $C_1$-$C_6$ alkyl, and $C_3$-$C_6$ cycloalkyl; and $R^1$ and $R^2$ or $R^3$ and $R^4$ may optionally be tethered together to form 3- to 7-membered alicyclic ring.

Another preferred embodiment of the present invention is represented by Formula 1, wherein A is —O— or —CH$_2$—; m and n vary independently and are an integer from 1 to 6; p and q vary from 0 to an integer from 1 to 3; B is —CR$^3$R$^4$; D is

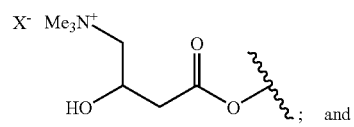

X is Cl or Br;

$R^1$ to $R^4$ are independently hydrogen or $C_1$-$C_6$ alkyl.

Another preferred embodiment of the present invention is represented by Formula 1, wherein: A is —O— or —H$_2$—; m is 4; n is 4; p varies from 0 to 3; q is 0 or 1; B is —R$^3$R$^4$; D is

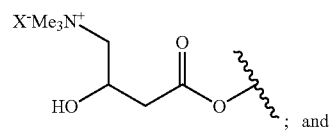

X is Cl or Br;

$R^1$ to $R^4$ are methyl groups.

Synthesis of the Compounds of the Invention

In the following process discussion, the following terms are defined as follows:

DCC means dicyclohexylcarbodiimide
DIBAL means diisobutyl aluminumhydride
DIEA means diethylamine
DIPEA means diisopropylethylamine
DMW means dimethyylforamide
DMPU means N,N'-dimethyl-N,N'-propylene urea
Et means ethyl
h. means hour(s)
Halogen means a chloro, bromo or iodo ion
HOBT means 1-hydroxybenzotriazole
IBA means isobutyric acid
LDA means lithium diisopropylamide
Me means methyl
Min(s). means minute(s)
MTBE means methyl-t-butyl ether
PDC means pyridiniumdichromate
PG means a protecting group such as t-butyl or a substituted or unsubstituted benzyl group;
Ph means phenyl
RP chromatography means reverse phase chromatography
RT means room temperature or ambient temperature, about 20-25° C.
TFA means trifluoroacetic acid
THF means tetrahydrofuran
p-TSA means p-toluenesulfonic acid The compounds belonging to Formula 1A as defined below can be synthesized according to the methodology illustrated in Schemes 1-8 below. These Schemes have 15 synthetic methods and novel intermediates that are useful in the preparation of the compounds of Formula 1 to obtain improved yields. These new features include the introduction of DL-, D-, or L-carnitine benzyl ester as a synthon in the conjugation step. Another improvement concerns the use of reverse phase chromatography to purify polar intermediates and products in good yields.

A dual prodrug compound or a pharmaceutically acceptable salt thereof of Formula 1A,

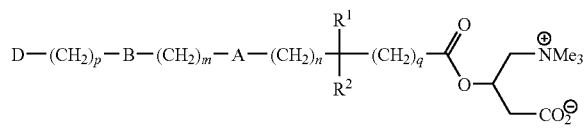

wherein A is selected from the group consisting of a single bond, —O—, or —CH$_2$—; m and n vary independently and are an integer from 1 to 15; p and q vary independently from 0 to an integer from 1 to 4; B is a single bond, or —CR$^3$R$^4$; D is selected from the group consisting of —C$_2$R$^5$, —OR$^6$, —OCOR$^7$, —SO$_3$R$^8$, —SO$_2$NH$_2$, —OPO(OR$^9$)(NH$_2$), —OPO(OR$^9$)—O—PO(OR$^{10}$)(OR$^{11}$),

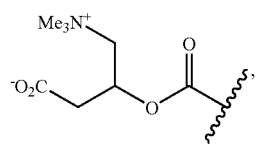

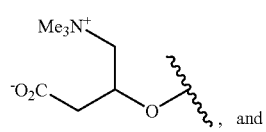
and

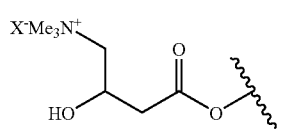

X is halogen;

R$^1$ to R$^{11}$ are independently selected from the group consisting of hydrogen; C$_1$-C$_6$ alkyl; C$_3$-C$_6$ cycloalkyl; C$_2$-C$_6$ alkenyl; C$_6$ alkynyl; C$_5$-C$_{10}$ aryl unsubstituted or substituted with C$_1$-C$_6$ alkyl, hydroxyl, C$_1$-C$_6$ alkoxyl, 1,3-dioxolanyl, cyano, halo, nitro, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, C$_1$-C$_6$ acylamino, mercapto, C$_1$-C$_6$ alkylthio, C$_1$-C$_6$ mercaptoalkyl, and C$_1$-C$_6$ alkoxycarbonyl; and C$_5$-C$_6$ arylalkyl unsubstituted or substituted with C$_1$-C$_6$ alkyl, hydroxyl, C$_1$-C$_6$ alkoxyl, 1,3-dioxolanyl, cyano, halo, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino; mercapto, C$_1$-C$_6$ alkylthio, C$_1$-C$_6$ mercaptoalkyl, and C$_1$-C$_6$ alkoxycarbonyl; C$_1$-C$_6$ carboxyalkyl; C$_1$-C$_6$ acylamino; C$_1$-C$_6$ sulfonatoalkyl; C$_1$-C$_6$ sulfamylalkyl; and C$_1$-C$_6$ phosphonatoalkyl.

Scheme 1
Synthesis of Compounds of Formula 1 is illustrated when m = n = 4, p = q = 0, A = —O— and D = —COOR$^5$ Step 1.

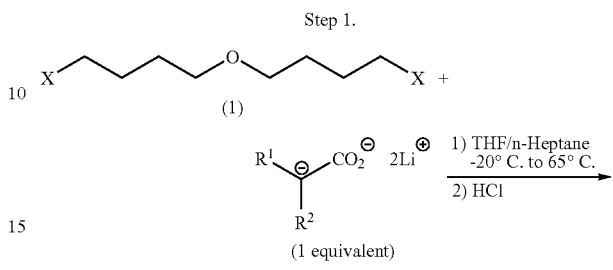

where X = halogen or any suitable leaving group; and R$^1$ and R$^2$ are defined as before;

Step 2.

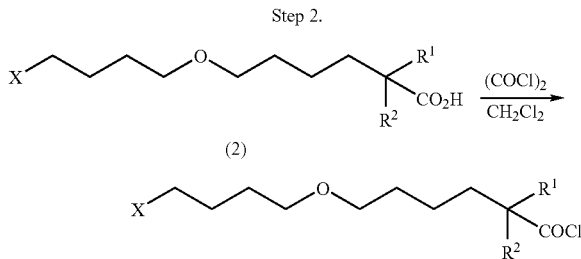

where R$^1$ and R$^2$ are defined as before;

Step 3.

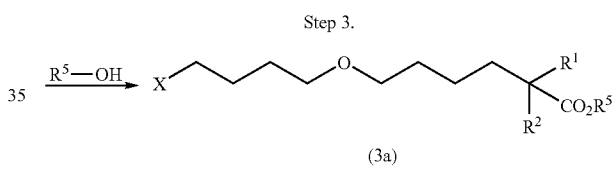

where R$^1$, R$^2$ and R$^5$ are defined as before;

Step 4.

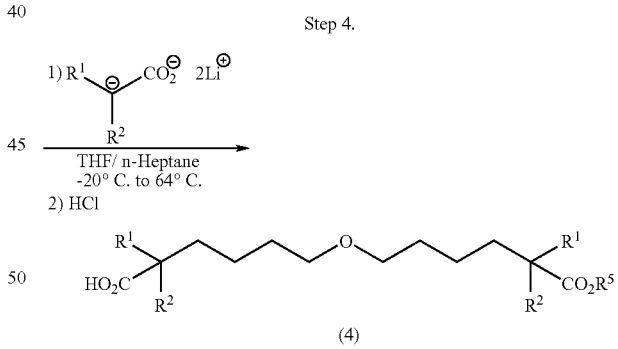

where R$^1$, R$^2$ and R$^5$ are defined as before;

Step 5.

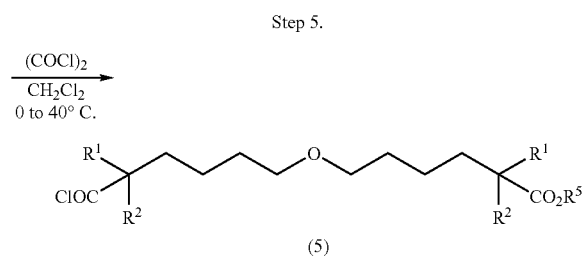

where R$^1$, R$^2$ and R$^5$ are defined as before;

-continued
Step 6.

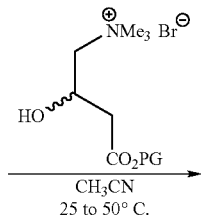

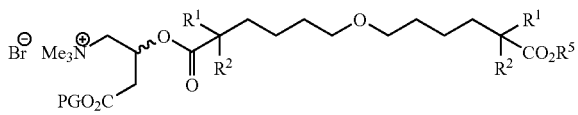

(6)

wherein PG is a protecting group chosen to be hydrogen, t-butyl, or a substituted or unsubstituted benzyl group i.e., $$\left( \begin{array}{c} \text{R}^1 \\ \text{R}^2 \end{array} \right)$$

, and $R^1$ and $R^2$ are as defined before for Formula 1, and carnitine may be of D, L, or DL configuration;

Step 7. When PG = 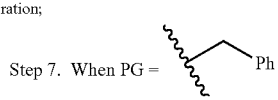

1) 10-20% Pd/C, $H_2$
   ──────────────→
   THF/$CH_3OH$
2) adjust pH
3) RP chromatography -continued

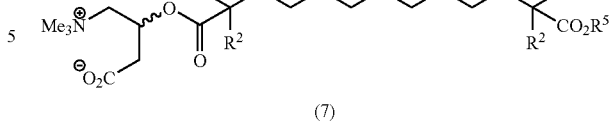

(7)

where $R^1$, $R^2$ and $R^5$ are defined as before;

If $R^5$ = 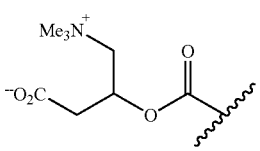 Ph, Step 7 above yields

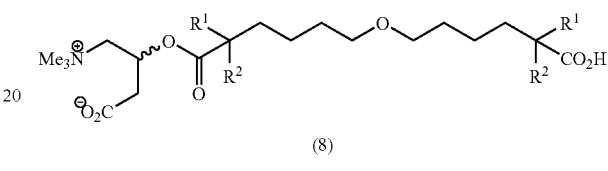

(8)

where $R^1$ and $R^2$ are defined as before;

Step 7. When PG = H, then carnitine may be directly coupled with acid chlorides.

The choice of solvent for this Scheme 1 is trifluoroacetic acid (TFA) which is needed to dissolve the polar carnitine betaine.

Scheme 2
Synthesis of Compounds of Formula 1 when m = n = 4, p = q = 0, A = —O— and D = -

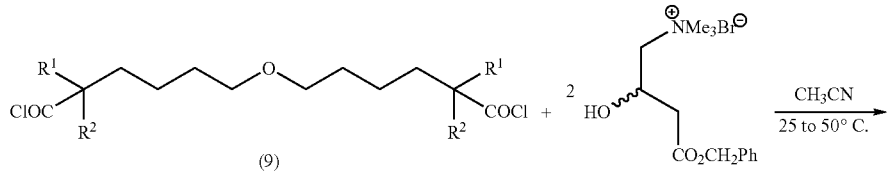

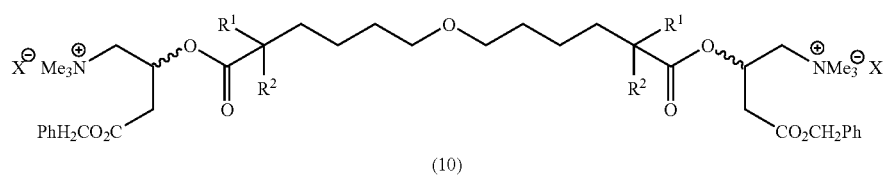

(10)

where X = Cl or Br; where $R^1$ and $R^2$ are defined as before;

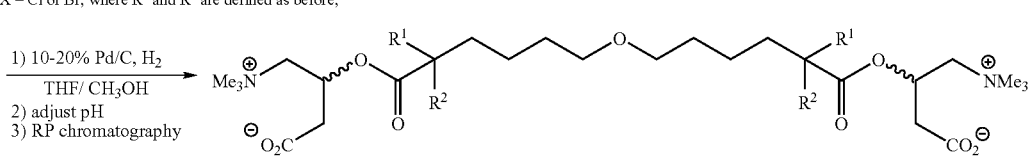

(11)

where $R^1$ and $R^2$ and are defined as before.

Scheme 3
Synthesis of Compounds of Formula 1 illustrated when m = n = 4; A =
—O—, p = q = 0, D = —OR⁶, —OCOR⁷, —SO₃R⁸, —SO₂NH₂,
—OPO(OR⁹)(OR¹⁰), —OPO(OR⁹)(NH₂), —OPO(OR⁹)—O—PO(OR¹⁰)(OR¹¹),
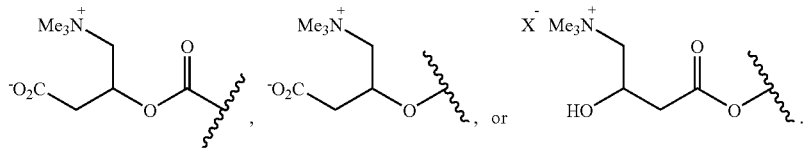
Step 1.
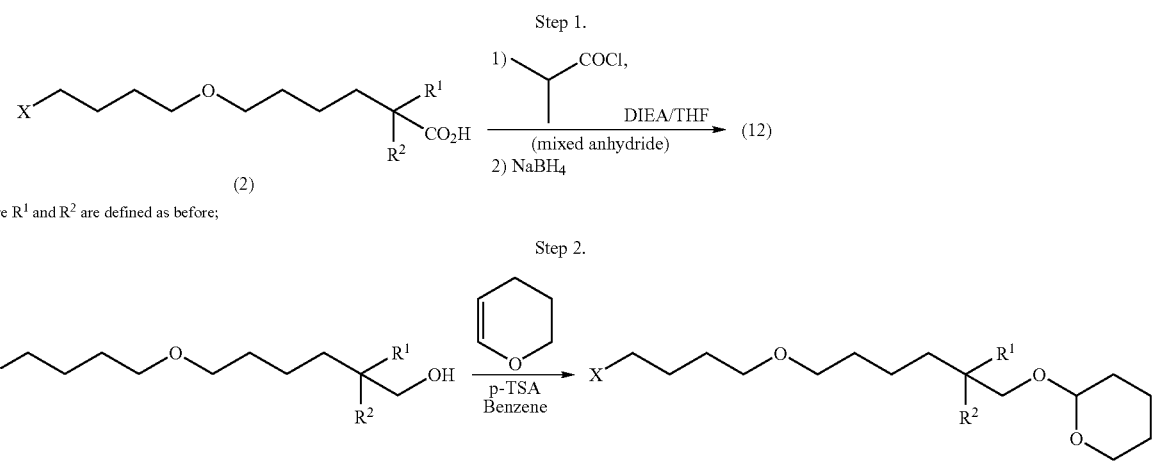
where R¹ and R² are defined as before;
Step 2.
where R¹ and R² are defined as before;
Step 3
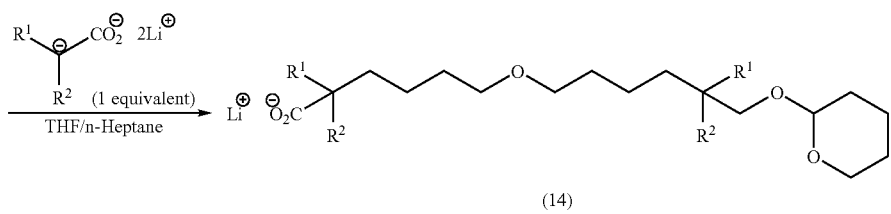
where R¹ and R² are defined as before;
Step 4.
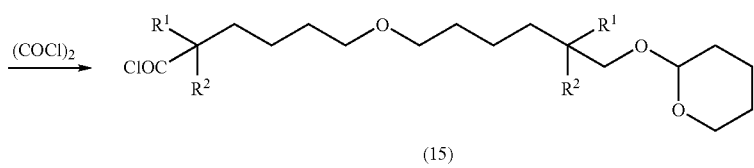
where R¹ and R² are defined as before;
Step 5.
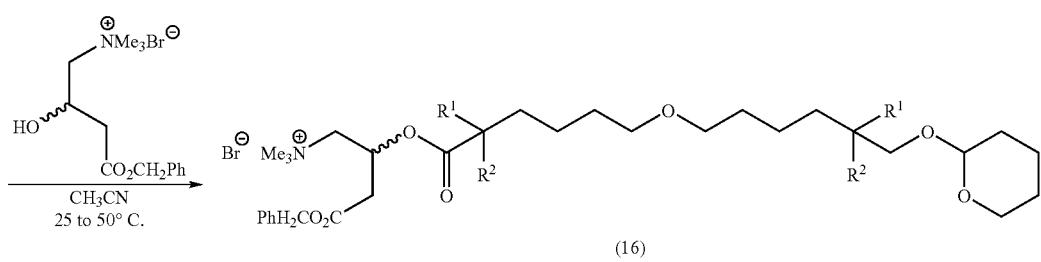
where R¹ and R² are defined as before;

-continued

Step 6.

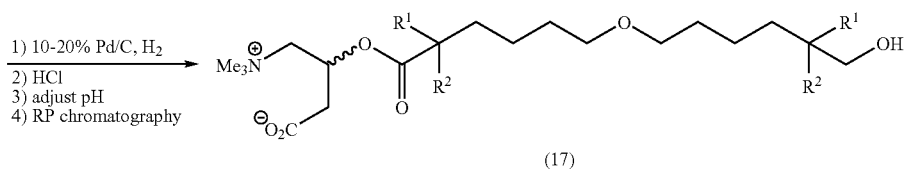

1) 10-20% Pd/C, H$_2$
2) HCl
3) adjust pH
4) RP chromatography (17)

where R$^1$ and R$^2$ are defined as before.

Alternatively,

Scheme 3a

Step 6.

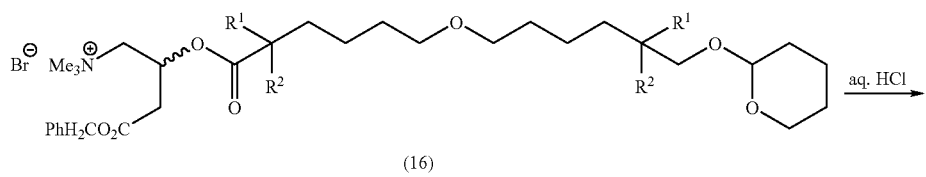

aq. HCl (16)

where R$^1$ and R$^2$ are defined as before;

Step 7.

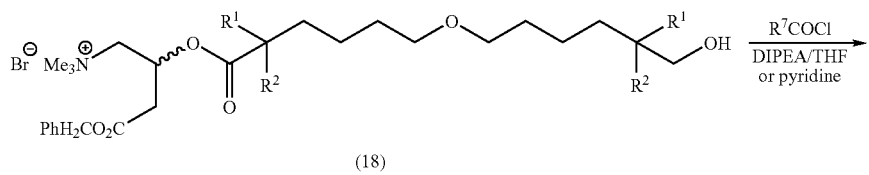

R$^7$COCl
DIPEA/THF
or pyridine (18)

where R$^1$, R$^2$ and R$^7$ are defined as before;

Step 8.

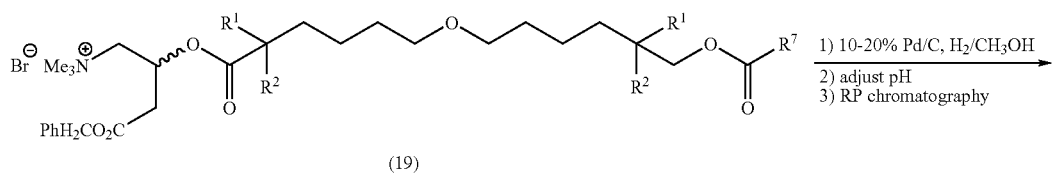

1) 10-20% Pd/C, H$_2$/CH$_3$OH
2) adjust pH
3) RP chromatography (19)

where R$^1$, R$^2$ and R$^7$ are defined as before;

Step 9

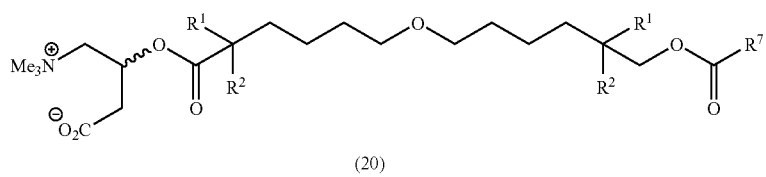

(20)

where R$^1$, R$^2$ and R$^7$ are defined as before.

Phosphate esters may similarly be prepared as above by synthetic methods well known in the art Alternatively,
Scheme 3b
Step 5.
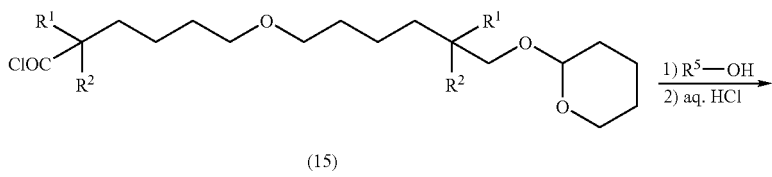
(15)
where $R^1$ and $R^2$ are defined as before;
Step 6.
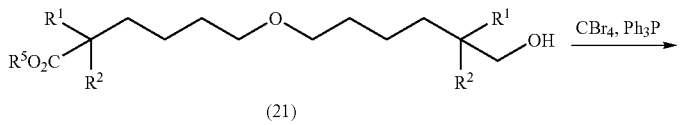
(21)
where $R^1$, $R^2$ and $R^7$ are defined as before;
Step 7.
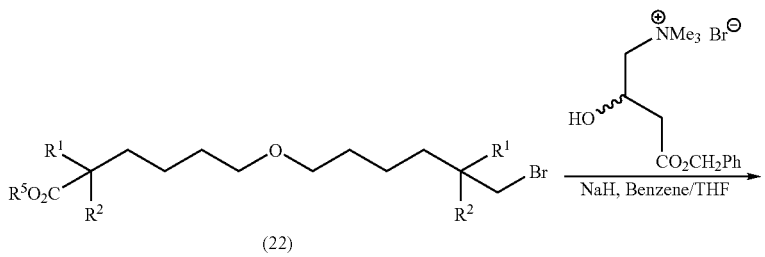
(22)
where $R^1$, $R^2$ and $R^7$ are defined as before;
Step 8.
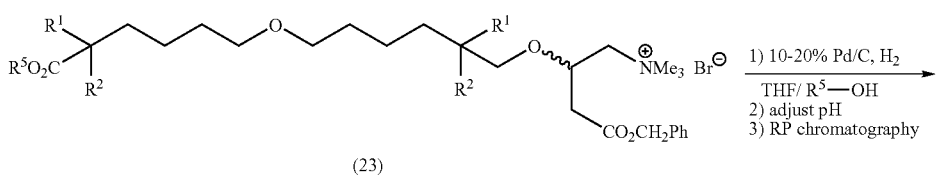
(23)
where $R^1$, $R^2$ and $R^7$ are defined as before;
Step 9.
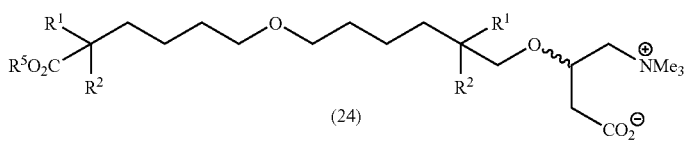
(24)
where $R^1$, $R^2$ and $R^7$ are defined as before.
Alternatively,
Scheme 3c
Step 7.
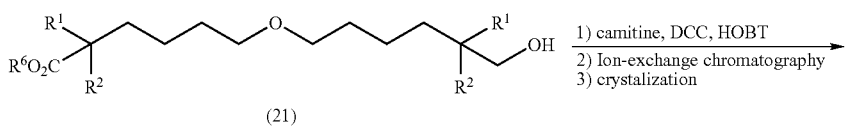
(21)
where $R^1$, $R^2$ and $R^5$ are defined as before;

Step 8.

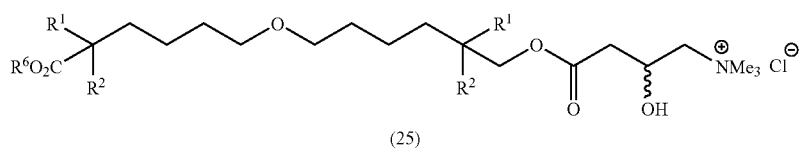

where $R^1$, $R^2$ and $R^5$ are defined as before.

Alternatively,

Scheme 3d

Step 1.

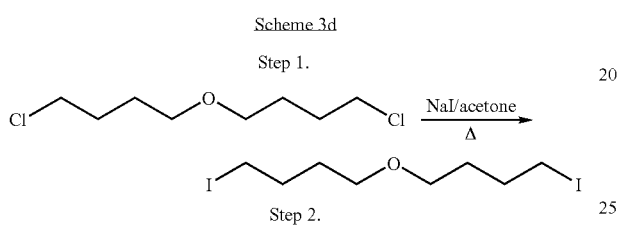

Step 2.

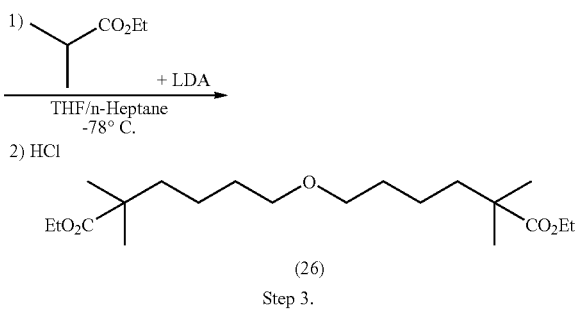

Step 3.

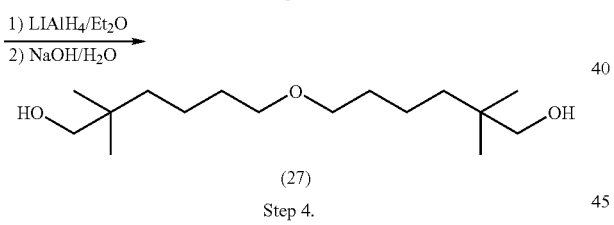

Step 4.

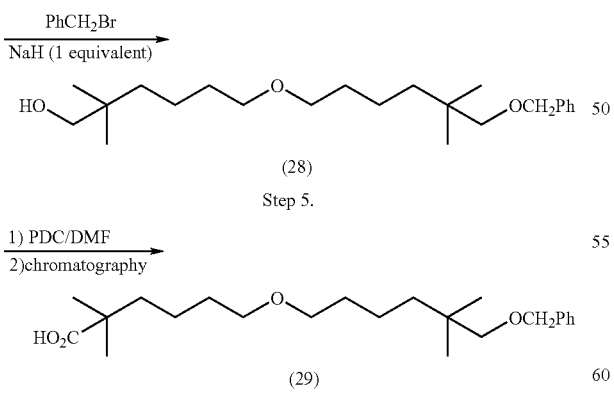

Step 5.

1) PDC/DMF
2) chromatography

Step 6.

1) SOCl₂
2) carnitine/TFA
3) H₂, Pd/C
4) RP chromatography

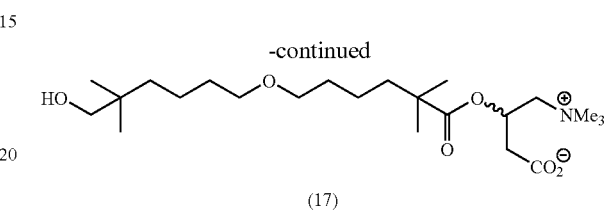

(17)

Scheme 4

DL-, D- and L-Carnitine benzyl esters and precursors are useful synthons which are prepared by the following schemes. [See Bohmer, T., et al., *Biochim. Biophys. Acta.* 152, 559-567 (1968); Strack, E., et al., *Hoppe-Seyter's Z. Physiol Chem* 343, 231-237 (1966); Konishi, M., et al., *J. Pharm. Sci.* 81, 1038-1041 (1992); Gaskell, D. S., et al., *Anal. Chem.* 58, 2801-2805 (1986).]

Scheme 4a

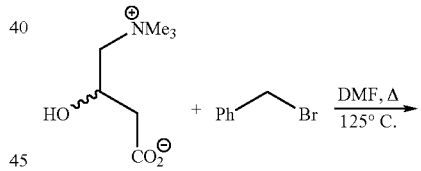

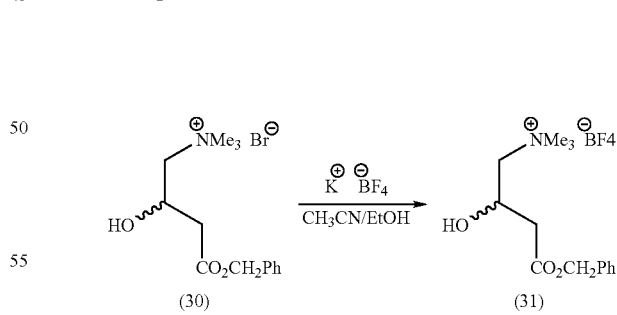

Scheme 4b

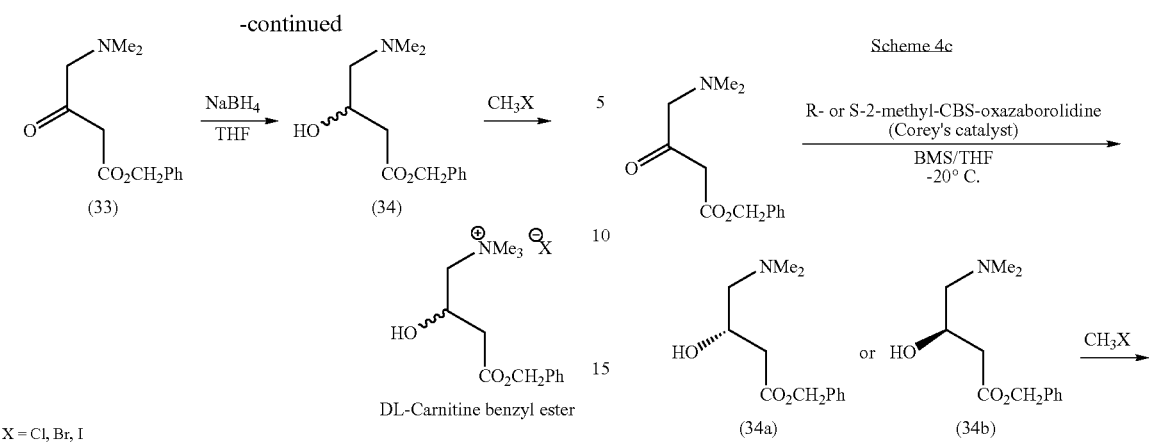
Alternatively, D- and L-carnitine benzyl esters may be prepared by Scheme 4c.
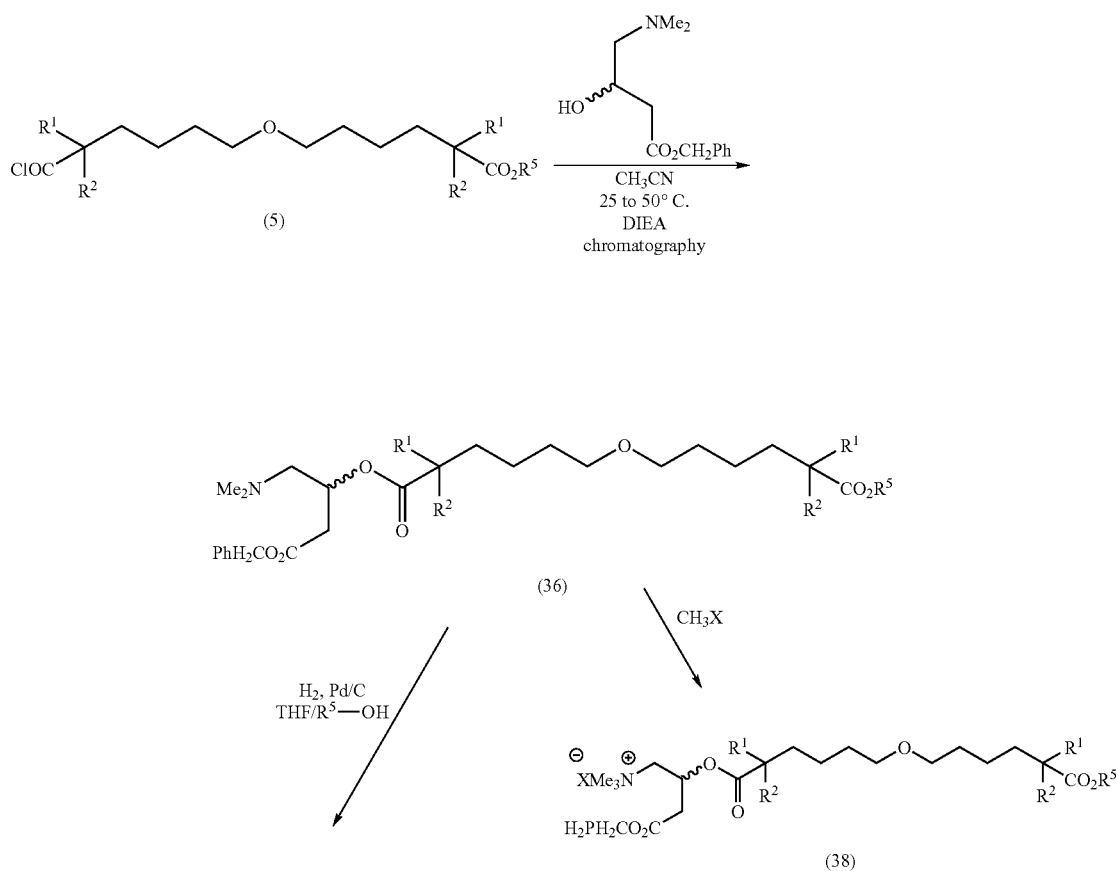
Scheme 5
Synthesis of Compounds of Formula 1 using novel DL-, D- or L-carnitine percursors as shown in Schemes 4b and 4c.
Step 5 in Scheme 1:

-continued
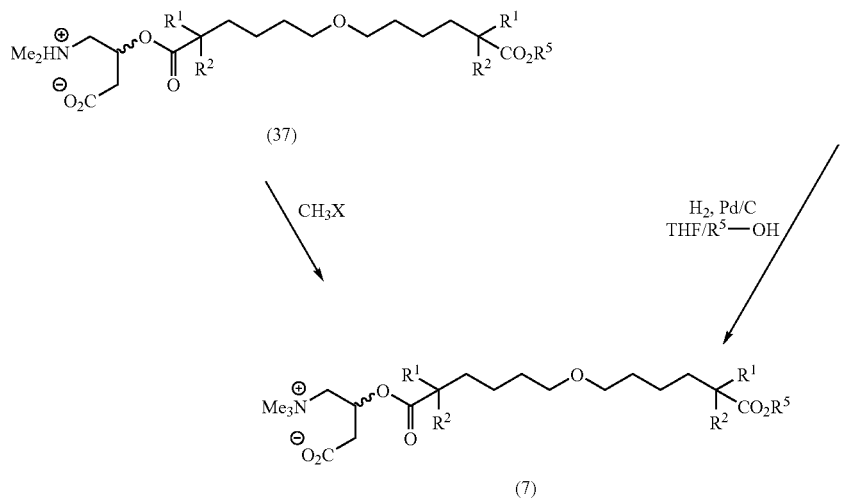
where $R^1$, $R^2$ and $r^5$ are defined as before.
Scheme 6
Synthesis of Compounds of Formula 1, where p, q = 1, A =
——O——, and m, n = 4 via Arndt-Eistert homologation sequence.
From Scheme 2,
Step 1.
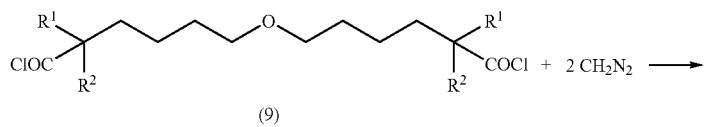
where $R^1$ and $R^2$ are defined as before;
Step 2.
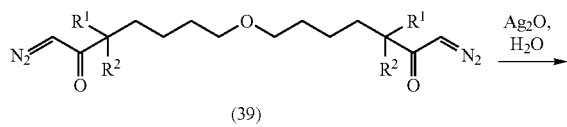
where $R^1$ and $R^2$ are defined as before;
Step 3.
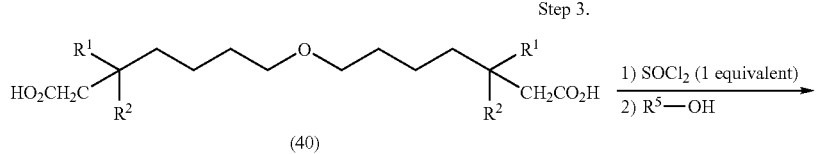
where $R^1$ and $R^2$ are defined as before;
Step 4.
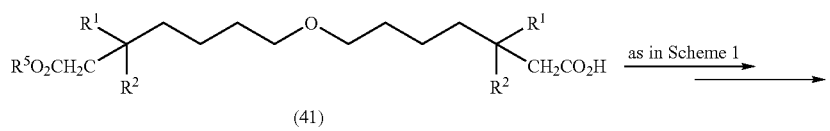
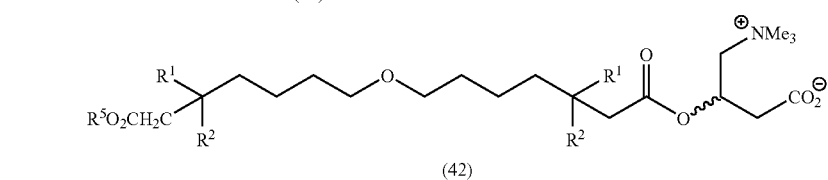
where $R^1$ and $R^2$ are defined as before.

Scheme 7
Synthesis of Compounds of Formula 1 where p, q = 1, A = —CH$_2$—, R$^1$, R$^2$ = CH$_3$
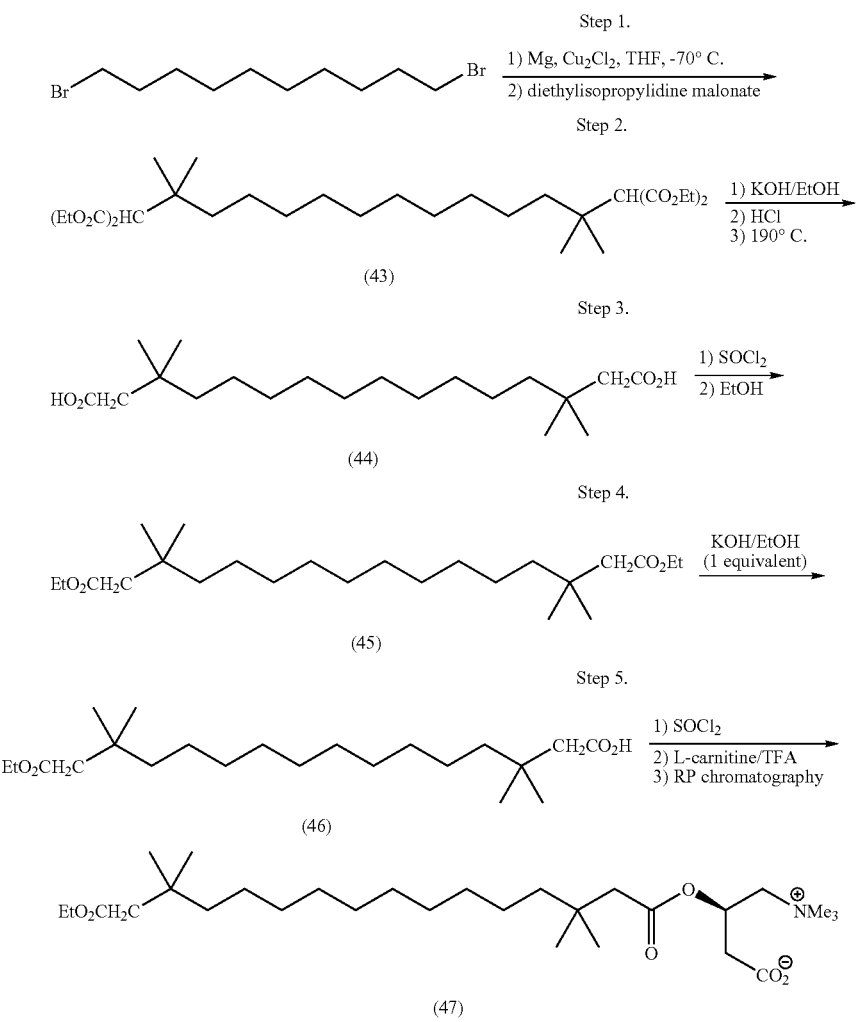
Scheme 8
Synthesis of Compounds of Formula 1, where p = 0, q = 1 (unsymmetrical ends), m, n = 4, A = —O—, and D = —CO$_2$R$^5$.
From Scheme 1 Step 5,
Step 1.
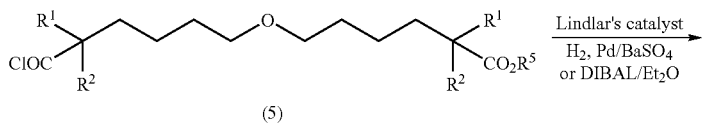
where R$^1$, R$^2$ and R$^5$ are defined as before;
Step 2.
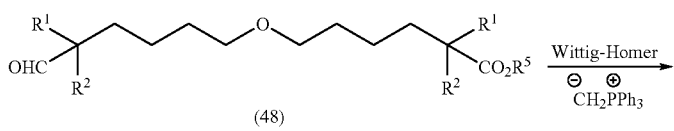
where R$^1$, R$^2$ and R$^5$ are defined as before;

-continued
Step 3.
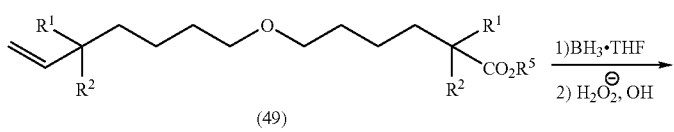
(49)
where $R^1$, $R^2$ and $R^5$ are defined as before;
Step 4.
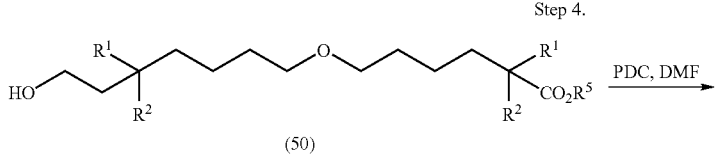
(50)
where $R^1$, $R^2$ and $R^5$ are defined as before;
Step 5.
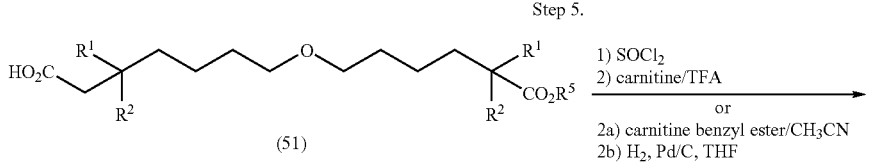
(51)
where $R^1$, $R^2$ and $R^5$ are defined as before;
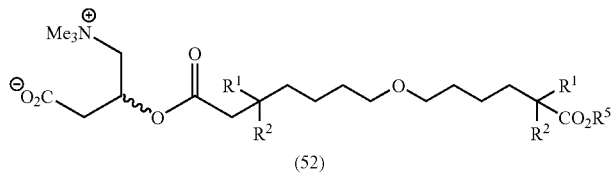
(52)
Alternatively,
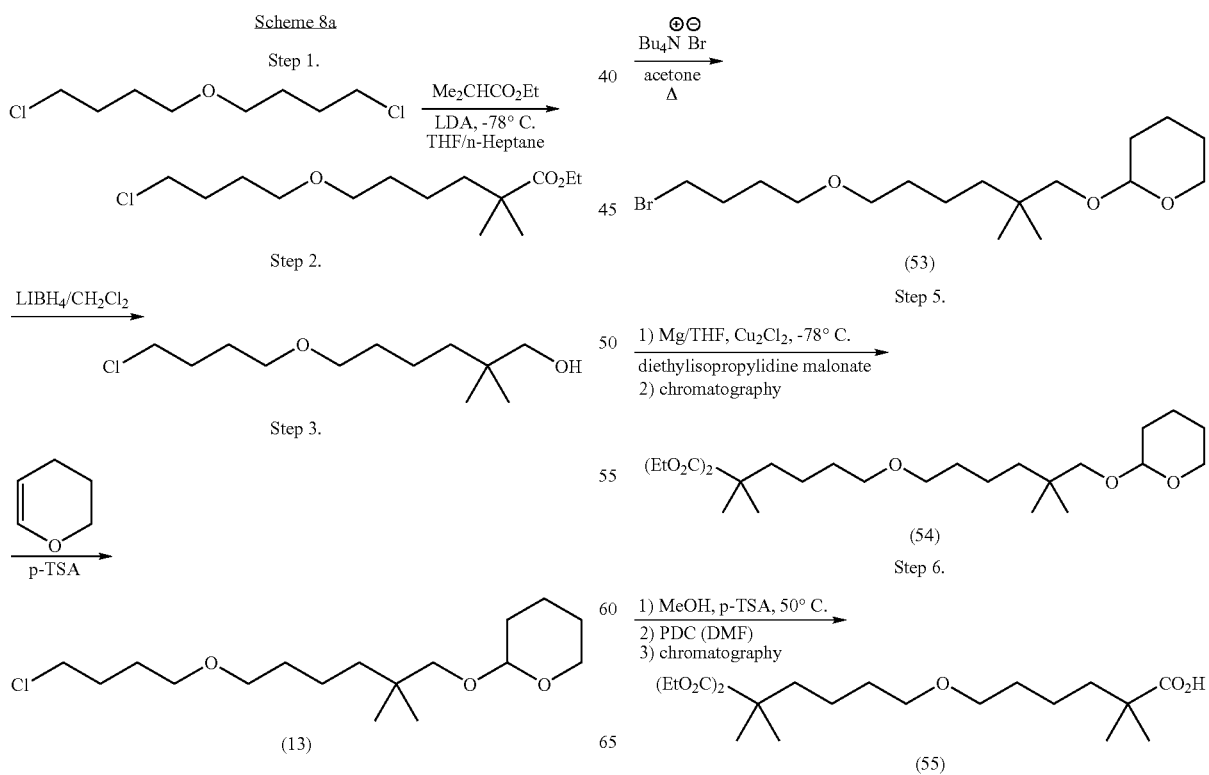

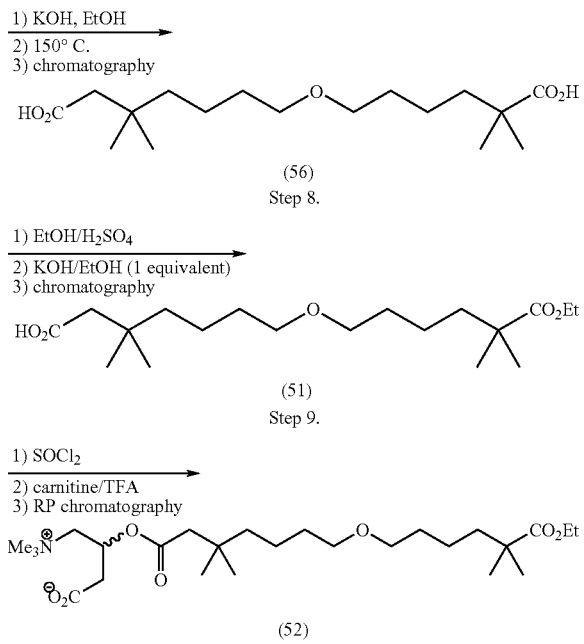

Compounds of Formula 1 may exist as a single stereoisomer or as a mixture of enantiomers and diastereomers whenever chiral centers are present. Individual stereoisomers can be isolated by the methods well know in the art: diastereomers can be separated by standard purification methods such as fractional crystallization or chromatography, and enantiomers can be separated either by resolution or by chromatography using chiral columns.

The pharmaceutical composition may also contain physiologically-acceptable diluents, carriers, adjuvants, and the like. The phrase "pharmaceutically-acceptable" means those formulations which are, within the scope of sound medical judgment, suitable for use in contact with the tissues of humans and animals without undue toxicity, irritation, allergic response and the like, and are commensurate with a reasonable benefit/risk ratio.

Pharmaceutically-acceptable salts are well-known in the art, and are described for example by Berge et al., *J. Pharm. Sci.* 66, 1-16 (1977), incorporated herein by reference. Representative salts include, but are not limited to acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate (isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calciwn, magnesium, aluminum, ammonium, tetramethyl ammonium, tetraethylammonium, methylammonium, dimethylammonium, trimethylammonium, triethylammonium, diethylammonium, and ethylammonium, and the like.

The pharmaceutical compositions of this invention can be administered to humans and other mammals enterally or parenterally in a solid, liquid, or vapor form. Parenteral route includes intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer.

The active compound is mixed under sterile conditions with a pharmaceutically-acceptable carrier along with any needed preservatives, excipients, buffers, or propellants. Ophthalmic formulations, eye ointments, powders and solutions are also contemplated as being within the scope of this invention. Actual dosage levels of the active ingredients in the pharmaceutical formulation can be varied so as to achieve the desired therapeutic response for a particular patient. The selected dosage level will depend upon the activity of the particular compound, the route of administration, the severity of the condition being treated, and prior medical history of the patient being treated.

The phrase "therapeutically effective amount" of the compound of Formula 1 means a sufficient amount of the compound to treat disorders, at a reasonable benefit/risk ratio applicable to medical treatment. It will be understood, however, that the total daily usage of the compounds and compositions of the present invention will be decided based on clinical experience. The specific therapeutically effective dose level for any particular patient will depend upon a variety of factors including the disorder being treated, the severity of the disorder; activity of the specific compound employed; the specific composition employed; age, body weight, general health, sex, diet of the patient; the time of administration, route of administration, and rate of excretion of the specific compound employed, and the duration of the treatment. The compounds of the present invention may also be administered in combination with other drugs, if medically thought necessary.

Compositions suitable for parenteral injection may comprise physiologically-acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer and the nature of the particular polymer employed, the rate of the drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration include powders, sprays, ointments, patch and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating arL They may optionally contain opacifying agents and may also be of a composition such that they release the active ingredient(s) only, or preferentially, in a certain part of the intestinal tract, optionally in a delayed manner. Examples of embedding compositions which can be used include polymeric substances and waxes. The active compounds can also be in micro-encapsulated form, if appropriate, with one of more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral suspending agents, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid are room temperature but liquid at body temperature and therefore melt in the rectum or vaginal cavity and release the active compound.

The present invention also provides pharmaceutical compositions that comprise compounds of the present invention formulated together with one or more non-toxic pharmaceutically-acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present invention compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art [see, for example, Prescott, Ed. *Methods in Cell Biology*, Vol XIV, pp. 33 et. seq. New York], incorporated herein by reference.

The examples which follow are presented to describe preferred embodiments and utilities of the invention and are not meant to limit the invention unless otherwise stated in the claims appended hereto. The description is intended as a non-limiting illustration, since many variations will become apparent to those skilled in the art in view thereof. Changes can be made in the composition, operation, and arrangement of the method of the present invention described herein without departing from the concept and scope of the invention as defined in the claims.

General Materials and Methods:

General: Commercial chemicals were treated as follows: THF distilled from Na/benzophenone; $CH_2Cl_2$ distilled over $CaH_2$. Bis(4-chlorobutyl)ether 98% (Lancaster); ethyl isobutyrate 99% (Acros Organics); benzyl isobutyrate 99% (Acros Organics); DCC 99% (Acros Organics), oxalyl chloride 2 M solution in $CH_2Cl_2$ (Acros Organics); LDA 2 M solution in THF/heptane (Acros Organics); benzyl bromide 98% (Acros Organics); DL-carnitine hydrochloride 99% (Acros Organics); L-carnitine inner salt 99+% (Acros Organics); preparation of L- and DL-carnitine benzyl ester salts are described below; propionyl chloride-functionalized silica gel, 1.0 mmol/g, 200-400 mesh (Aldrich), acetonitrile anhydrous (99.9%) were used as received.

Other materials not listed above were used as received.

Chromatography media: silica gel (J. T. Baker, 60-200 mesh, TLC plates Analtech GF, cat number 2521 or Merck 60, number 4715.

NMR spectra were obtained on a Bruker Advance 200 spectrometer.

IR spectra were recorded on a Bio Rad FTS-175C.

The $^1H$ and $^{13}C$ NMR chemical shifts are in δ and ppm, respectively, and J values are in Hz.

Mass spectra were recorded on a Finnigan Mat 95 high resolution and a Hewlett Packard 5973 GC/MS instruments.

Microanalyses were conducted by Atlantic Microlab.

Melting points were recorded on Büchi apparatus, using sealed capillaries.

The following procedures, indicated by lettered examples, were used to make some of the starting materials used in the following examples. All others were purchased.

EXAMPLE A

L-carnitine benzyl ester bromide

A suspension of L-carnitine inner salt (0.8051 g, 5.000 mmol) and benzyl bromide (0.72 mL, 6.00 mmol) in DMF (10 mL) was heated oil bath at 125° C. (oil bath) under nitrogen for 8 h (solid of carnitine gradually dissolved). The solvent was removed by rotary evaporation and the residue was kept in vacuum (oil pump) for 1 h. The solid was washed with ethyl ether (2×5 mL). The remaining solid (1.50 g) was recrystallized from anhydrous acetonitrile to give L-carnitine benzyl ester bromide (1.30 g, 3.91 mmol, 78%), mp 184-187° C.

IR (KBr) 3257, 3006, 1732, 1490, 1320, 1180, 1083, 958 cm$^{-1}$.

NMR: $^1$H (200 MHz, D$_2$O) 7.44 (s, 5H C$_6$H$_5$), 5.19 (d, J=2.9, 2H, CH$_2$ benzyl), 4.76-4.58 (m, 1H, CH), 3.50-3.39 (m, 2H, CH$_2$N), 3.17 (s, 9H, N(CH$_3$)$_3$), 2.75-2.62 (m, 2H, CH$_2$COO); $^{13}$C (50 MHz, D$_2$O and acetonitrile as internal reference) 172.3, 135.9, 129.5, 129.3, 129.0, 70.1, 67.9, 63.3, 54.7, 40.7.

MS (FAB, methanol) (positive) 252 (100%, M$^+$).

EXAMPLE B

DL-carnitine benzyl ester bromide

A solution of DL-carnitine hydrochloride (2.164 g, 10.93 mmol) and sodium hydroxide (0.6561 g, 16.41 mmol) in EtOH (32A mL) was stirred at RT for 2 h. The resulting white solid (NaCl) was removed by filtration, and the solvent was removed under reduced pressure to give a white solid. That was dried over P$_2$O$_5$ in vacuum (oil pump) for 5 h. A suspension of the DL-carnitine inner salt and benzyl bromide (2.240 g, 13.11 mmol) in DMW (20 mL) was heated at 125° C. under nitrogen for 8 h (solid of carnitine gradually dissolved). The solvent was removed by rotary evaporation and the residue was kept in vacuum (oil pump) for 1 h. The solid was washed with ethyl ether (2×20 mL). The remaining solid (3.9550 g) was recrystallized from anhydrous acetonitrile to give DL-carnitine benzyl ester bromide (3.050 g, 9.182 mmol, 84%), mp 164-167° C.

IR (Kr) 3254, 1733, 1453, 1412, 1320, 1184 cm$^{-1}$.

NMR: $^1$H (200 Mz, D$_2$O) 7.51-7.32 (m, 5H C$_6$H$_5$), 5.19 (d, J=2.9, 21, CH$_2$C$_6$H$_5$), 4.75-4.55 (m, 1H, CH), 3.45-3.38 (m, 2H, CH$_2$N), 3.16 (s, 9H, N(CH$_3$)$_3$), 2.76-2.64 (m, 2H, CH$_2$COO).

EXAMPLE C

L-carnitine benzyl ester tetrafluoroborate

L-carnitine benzyl ester bromide (0.2022 g, 0.6164 mmol) was dissolved in a mixture of acetonitrile (10 mL) and EtOH (2 mL). A solution KBF$_4$ (0.3880 g, 3.0823 mmol) acetonitrile (5 mL) and EtOH (1 mL) was added at RT and stirred for 12 h. Solid was filtered off and the filtrate was evaporated to dryness. White solid was dried over P$_2$O$_5$ in vacuum (oil pump) for 2 h and recrystallized from CH$_2$Cl$_2$ and ethyl ether (4:1). Tetrafluoroborate salt of L-carnitine benzyl ester (0.1250 g, 0.3686 mmol, 60%) mp 152-156° C. was obtained.

IR (KBr) 3255, 1732, 1488, 1322, 1183, 1078, 768, 726, 646 cm$^{-1}$.

EXAMPLE D

DL-carnitine benzyl ester tetrafluoroborate

DL-carnitine benzyl ester bromide (0.2022 g, 0.6164 mmol) was dissolved in a mixture of acetonitrile (10 mL) and EtOH (2 mL) and solution KBF$_4$ (0.3880 g, 3.0823 mmol) in acetonitrile (5 mL) and EtOH (1 mL) was added at RT and stirred for 12 h. Solid filtered off and filtrate was evaporated to dryness. White solid was dryness over P$_2$O$_5$ in vacuum (oil pump) for 2 h and recrystallized from dichloromethane and ethyl ether (4:1). Tetrafluoroborate salt of DL-carnitine benzyl ester (0.1234 g, 0.3638 mmol, 59%), mp 144-148° C. was obtained.

IR (KBr) 3255, 1727, 1483, 1313, 178, 1082 cm$^{-1}$.

The following examples are those of the invention.

EXAMPLE 1 a. 4-Chlorobutoxy)-2,2-dimethylhexanoic acid, (2), Scheme 1, R$^1$, R$^2$ are —CH$_3$ To a solution of isobutyric acid (IBA) (1.85 & 21.0 mmol) in anhydrous THF (15 mL), lithium diisopropylamide (LDA) (2.0 M in THF/hexanes; 21 mL, 42 mmol) was added dropwise at −30° C. under N$_2$ atmosphere. In a separate flask 4-chlorobutyl ether (4.1815 g, 21.000 mmol) was dissolved in THF (10 mL) and cooled to −10° C. (N$_2$ atmosphere). To this solution, dilithium isobutyrate was transferred (canula), slowly (30 min), and the reaction mixture was stirred for 1 h at −10° C. Reaction mixture was allowed to reach RT. After 1 h the mixture was refluxed for 30 min, cooled down to RT, and quenched with ice-water (2 mL). Organic layer was extracted with water (20 mL). Combined last two aqueous layers were extracted with ether (20 mL). Aqueous layer was acidified with diluted HCl to pH=3 and extracted with ether (2×20 mL). Combined last two ether extracts were dried over Na$_2$SO$_4$ and solvent was removed to give crude 6-(4-chlorobutoxy)-2,2-dimethylhexanoic acid as an oil (5.253 g).

R$_f$=0.28 (hexane/ethyl acetate, 4:1 v/v).

IR (CHCl$_3$) 2934, 1706, 1411, 1291, 1172 cm$^{-1}$.

$^1$H NMR (200 Mz, CDCl$_3$, δ) 9.12 (s, broad 1H, COOH), 3.57 (t, 2H, CH$_2$Cl), 3.44 (t, 2H, CH$_2$C(CH$_3$)$_2$), 3.38 (t, 4H, 2CH$_2$O), 1.62-1.23 (m, 8H, 2CCH$_2$CH$_2$C), 1.20 (s, 6H, 2CH$_3$).

b. 6(4-Chlorobutoxy)-2,2-dimethylhexanoyl chloride, (3), Scheme 1, R$^1$, R$^2$ are —CH$_3$ Crude 6-(4-chlorobutoxy)-2,2-dimethylhexanoic acid (2.62 g) was dissolved in CH$_2$Cl$_2$ (5 mL), and reaction mixture was cooled to 5° C. Oxalyl chloride (2 M solution in CH$_2$Cl$_2$); 10.0 mL, 20 mmol) was added with stirring under N$_2$. The mixture was allowed to warm up to RT. After 30 min, flier amount of oxalyl chloride (10.0 mL, 20 mmol) was added. The solution was stirred for 2 h, concentrated under reduced pressure (25° C./10 mm Hg). The oil residue was dissolved in CH$_2$Cl$_2$ (5 mL) and concentrated in the same way to yield 6-(4-chlorobutoxy)-2,2-dimethylhexanoyl chloride as oil (1.69 g, 6.48 mmol).

IR (CH$_{12}$Cl$_2$) 2930, 1777, 1410, 1291, 1179 cm$^{-1}$.

$^1$H NMR (200 MHz, CDCl$_3$, δ) 3.59 (t, 2H, CH$_2$Cl), 3.41 (t, 2H, CH$_2$C(CH$_3$)$_2$), 3.40 (t, 4H, 2CH$_2$O), 1.62-1.20 (m, 8H, 2CCH$_2$CH$_2$C), 1.22 (s, 6H, 2CH$_3$).

c. Ethyl 6(4-chlorobutoxy)-2,2-dimethylhexanoate, [(3a), Scheme 1, R$^5$=Et, R$^1$, R$^2$ are —CH$_3$]

EtOH (0.69 g, 15 mmol) in CH$_2$Cl$_2$ (5 mL) was added dropwise at RT to 6-(4-chlorobutoxy)-2,2-dimethylhexanoyl chloride (1.69 g, 6.28 mmol). The reaction mixture was stirred for 12 h. Solvent was removed under reduced pressure (25° C./10 mm Hg) to give ethyl 6-(4-chlorobutoxy)-2,2-dimethylhexanoate as an oil (1.577 gm 5.662 mmol, 90%).

IR(CHCl$_3$) 2943, 1719, 1474, 1259, 1150 cm$^{-1}$.

$^1$H NMR (200 MHz, CDCl$_3$, δ) 4.12 (q, 2H, CH$_2$CH$_3$), 3.57 (t, 2H, CH$_2$Cl) 3.42 (t, 2H, CH$_2$C(CH$_3$)$_2$), 3.38 (t, 4H, 2CH$_2$O), 1.62-1.18 (m, 14H, C(CH$_3$)$_2$, 2CCH$_2$CH$_2$C), 1.24 (t, 3H, CH$_2$CH$_3$).

d. 6-(6-Ethoxy-5,5-dimethyl-6-oxohexanoxy)-2,2-dimethylhexanoic acid, [(4), Scheme 1, R$^5$-Et, R$^1$, R$^2$ are —CH$_3$]

To a solution of isobutyric acid (IBA) (0.5138 g, 5.832 mmol) in anhydrous THF (5 mL) lithium diisopropylamide (LDA) (2.0 M in THF/hexanes; 5.83 mL, 12.0 mmol) was added dropwise at −20° C. under N$_2$ atmosphere. A separate flask was charged with ethyl 6(4-chlorobutyl)-2,2-dimethylhexanoate (1.624 g, 5.832 mmol) and THF (15 mL), and the mixture was cooled to −20° C. Dilithium isobutyrate was transferred (canula) under N$_2$ to the main flask, slowly for 2 h, with stirring. Reaction mixture was stirred for 1 h (−20° C.), and at RT for 8 h. The mixture was cooled to 0° C., and cold water (15 mL) was added. The reaction mixture was extracted with ether (2×20 mL). Water layer was acidified with diluted HCl to pH=3 and extracted with ether (2×10 mL). Solvent was removed by rotary evaporation (25° C./10 mm Hg) to give crude 6-(6-ethoxy-5,5-dimethyl-6-oxohexanoxy)-2,2-dimethylhexanoic acid as an oil (1.24 g).

R$_f$=0.19 (hexane/ethyl acetate, 9:1 v/v).

IR (CH$_2$Cl$_2$) 2944, 1704, 1475, 1150, 1127 cm$^{-1}$.

$^1$H NMR (200 MHz, CDCl$_3$, δ) 920 (br s, 1H, COOH), 4.12 (q, 2H, CH$_2$CH$_3$), 3.46-3.33 (m, 8H, 2CH$_2$C(CH$_3$)$_2$, 2CH$_2$O), 1.62-1.12 (m, 23H, 2C(CH$_3$)$_2$, 2CH$_2$CH$_2$C, CH$_2$CH$_3$).

e. 6-(6-Ethoxy-5,5-dimethyl-6-oxohexanoxy)-2,2-dimethylhexanoyl chloride, (5) Scheme 1, R$^5$=Et, R$^1$, R$^2$ are —CH$_3$ Crude 6-(6-ethoxy-5,5-methyl-6-oxohexanoxy)-2,2-dimethylhexanoic acid (1.24 g) was dissolved in CH$_2$Cl$_2$ (15 mL), and the mixture was cooled to 0° C. Oxalyl chloride (2 M solution in CH$_2$Cl$_2$; 9.0 mL, 18.0 mmol) was added slowly with stirring under N$_2$. The mixture was allowed to warm up to RT. After 30 min at RT, a further amount of oxalyl chloride (9.0 mL, 18.0 mmol) was added. The resulting solution was stirred for 2 h at RT and concentrated under reduced pressure (25° C./10 mm Hg) to give 6-(6-ethoxy-5,5-dimethyl-6-oxohexanoxy)-2,2-dimethylhexanoyl chloride as oil (0.99 g, 2.9 mmol).

IR(CH$_{12}$Cl$_2$) 2945, 1782, 1719, 1472, 1148, 1113 cm$^{-1}$.

$^1$H NMR (200 MHz, CDCl$_3$, δ) 4.12 (q, 2H, CH$_2$CH$_3$), 3.45-3.31 (m, 8H, 2CH$_2$C(CH$_3$)$_2$, 2CH$_2$O), 1.64-1.12 (m, 23H, 2CCH$_2$CH$_2$C, CH$_2$CH$_3$).

f. 6-(6-Ethoxy-5,5-dimethyl-6-oxohexanxy)-2,2-dimethylhexanoyl-carnitine benzyl ester chloride, (6), Scheme 1, R$^5$=Et, R$^1$, R$^2$ are CH$_3$, X=Cl, PG=—CH$_2$Ph.

A flask was charged with 6-(6-(ethoxy-5,5-dimethyl-6-oxohexanoxy)-2,2-dimethylhexanoyl chloride (0.31 g, 0.88 mmol), L-carnitine benzyl ester bromide (0.32.1 g, 0.966 mmol), and acetonitrile (5 mL). Reaction mixture was heated at 65° C. for 18 h under N$_2$. Carnitine benzyl ester bromide gradually dissolved. Solvent was removed under reduced pressure. The oil residue was washed with ether (2×5 mL) and dissolved in CHCl$_3$ (5 mL), and ether (5 mL) was added to precipitate. The mixture was kept in the freezer (−15° C.) for 12 h and solid was filtered off. Solvent was removed from filtrate by rotary evaporation to give 6-(6-ethoxy-5,5-dimethyl-6-oxohexanoxy)-2,2-dimethylhexanoyl-L-carnitine benzyl ester chloride as an oil (0.493 g).

R$_f$=0.63 (chloroform/ethanol, 4:1 v/v).

IR (CHCl$_3$) 2943, 1730, 1477, 1147, 1127 cm$^{-1}$.

$^1$H NMR (200 MHz, CDCl$_3$, δ) 7.34 (s, C$_6$H$_5$), 5.79-5.55 (m, 1H, CH), 5.12 (s, 2H, CH$_2$C$_6$H$_5$), 4.40-3.85 (m, 4H, NCH$_2$, CH$_2$CH$_3$), 3.72-2.65 (m, 19H, N(CH$_3$)$_3$, 2CH$_2$C(H)$_2$, CH$_2$COO, 2CH$_2$O), 1.70-0.96 (m, 23H, 2C(CH$_3$)$_2$, 2CCH$_2$CH$_2$C, CH$_2$CH$_3$).

EXAMPLE 2

Alternative Synthesis of (6) in the Above Example 1, Via Scheme 3d a. 4'-Chloro-4-iododibutyl ether 4,4'-Dichlorodibutyl ether (15.0 g, 75.3 mmol) was added to a solution of sodium iodide (11.3 g, 75.3 mmol) in dry acetone (300 mL) and the mixture was refluxed. Progress of the reaction was monitored by $^1$H and $^{13}$C NMR. After 11.5 hr, the precipitate was filtered, and washed with acetone (2×30 mL). Solvent was evaporated under reduced pressure from the combined filtrates. Light yellow oil residue was dissolved in ethyl ether (70 mL), washed with water (50 mL), sodium thiosulphate (2%, 30 mL), and water (30 mL), and dried over Na$_2$SO$_4$. Solvent was removed by rotary evaporation, and the residue was distilled in vacuum. Four fractions were collected: fraction I, 2.5 g, b.p. 75-79° C./0.1 mm Hg; fraction II, 2.4 g, b.p. 79-83° C./0.1 mm Hg; fraction III, 10.59 g, b.p. 85-89° C./0.1 mm Hg; fraction IV, 4.9 g, b.p. 92-109° C./0.1 mm Hg.

Fractions I and II of were identified as a mire of dichloro- and chloroiodobutyl ethers. Fraction IV was identified as mixture of chloroiodo- and diiodobutyl ethers. Fraction III was identified as pure chloroiodobutyl ether (10.59 g, 36.5 mmol, 49%), b.p. 85-89° C./0.1 mm Hg.

IR (CH$_2$Cl$_2$) 2943, 2868, 1446, 1373, 1226, 1113 cm$^{-1}$.

NMR $^1$H (200 MHz, CDCl$_3$) 3.58 (t, J=6.3, 2K, CH$_2$Cl), 3.44 (t, J=6.2, 4H, 2CH$_2$O), 3.23 (t, J=6.8, 2H, CH$_2$I), 2.06-1.5 (m, 8H, 2CCH$_2$CH$_2$C), $^{13}$C (50 MHz, CDCl$_3$) 70.1, 69.8, 45.1, 30.7, 30.6, 29.7, 27.2, 7.1.

MS (m/z) 183, 163, 155, 91, 85, 73, 55.

b. Ethyl 6-(4'-chlorobutoxy)-2,2-dimethylhexanoate

Ethyl isobutyrate (2.595 g. 22.37 mmol) and DMPU (0.02 mL) were dissolved THF (25 mL) and cooled to −78° C. (acetone/dry ice). LDA (9.47 mL) was added dropwise, and reaction mixture was stirred in this temperature for 1 h. In a separate flask 4'-chloro-4-iododibutyl ether (5.000 g, 17.21 mmol) was dissolved in THF (25 mL) and cooled to −78° C. To this solution lithium ethyl isobutyrate was transferred (cannula) under N$_2$, slowly (1 h) with stirring, and the reaction mixture was stirred for additional 1 h at −78° C. After 12 h the reaction mixture was allowed to reach −5° C. The cold solution was quenched with ice/water and diluted HCl (25 mL, pH=4), and ethyl ether (20 mL) was added. Layers were separated, and water layer was extracted with ethyl ether (20 mL). Combined organic layer were dried over $Na_2SO_4$ and solvent was removed by rotary evaporation. The residue was distilled in vacuum, and the fraction of b.p. 98-100° C./0.9 mmHg was collected to give ethyl 6-4'-chlorobutoxy)-2,2-dimethylhexanoate (4.17 g, 15.0 mmol, 670%).

IR ($CH_2Cl_2$) 2943, 2868, 1716, 1474, 1365, 1148, 1113 $cm^{-1}$.

NMR: $^1H$ (200 z, $CDCl_3$) 4.14 (q, J=7.1, 2H, $CH_2CH_3$), 3.57 (t, J=6.3, 2H, $CH_2Cl$), 3.43 (t, J=6.3, $OCH_2CH_2$), 3.39 (t, J=6.6, $OCH_2CH_2$), 1.95-1.45 (m, 8H, 2 $CCH_2CH_2C$), 1.35-1.12 (m, 11H, $CH_2C(CH_3)_2$, $CH_2CH_3$); $^{13}C$ (50 MHz, $CDCl_3$) 179.5, 72.1, 71.3, 61.6, 46.4, 43.6, 41.9, 31.6, 31.0, 28.9, 26.5, 23.0, 15.7.

MS (CI) (isobutane) $M^+$ 279 (100%). Calc for $C_{14}H_{27}ClO_3$: C, 60.32; 9.76.

Found: C, 61.82; H. 9.74.

c. Ethyl 6-(4'-iodobutoxy)-2,2-dimethylhexanoate

Ethyl 6-(4'-chlorobutoxy)-2,2-dimethylhexanoate (4.00 g, 14.4 mmol) and NaI (2.810 g, 18.72 mmol) were refluxed in acetone. Progress of reaction was monitored by $^1H$ NMR. No loss of Et group from the ester was observed over the t course of 72 h. Solvent was evaporated under reduced pressure. Light yellow oil residue was dissolved in ethyl ether (70 mL), washed with water (50 mL), sodium thiosulphate (2%, 30 mL), water (30 mL), and dried over $Na_2SO_4$. Solvent was removed, and the residue was distilled in vacuum. Fraction b.p. 110-112° C./0.4 mm Hg gave ethyl 6-(4'-iodobutoxy)-2,2-dimethylhexanoate (4.952 g, 13.38 mmol, 93%).

IR($CH_{2C4-2}$)2942, 2868, 1719, 1470, 1386, 1362, 1226, 1151, 1111 $cm^{-1}$.

NMR: $^1H$ (200 MHz, $CDCl_3$) 4.11 (q, J=7.2, 2H, $CH_2CH_3$), 3.42 (t, J=6.2, 2H, $CH_2O$), 3.38 (t, J=6.8, 2H, $CH_2O$), 3.22 (t, J=6.9, 2H, $CH_2I$), 1.95-1.4S (m, 8H, 2 $CCH_2CH_2C$), 1.35-1.12 (m, 11H, $CH_2C(CH_3)_2$, $CH_2CH_3$); $^{13}C$ (50 MHz, $CDCl_3$) 178.2, 70.9, 69.8, 60.4, 42.3, 40.7, 30.8, 30.6, 30.4, 25.3, 21.8, 14.5, 7.1.

MS (CI) (isobutane), 371 (100%, $M^+$).

d. 6-(6-Ethoxy-5,5-dimethyl-6-oxohexanoxy)-2,2-dimethylhexanoic acid

Isobutyric acid (1.145 g. 13.00 mmol) was dissolved in THF (25 mL) and cooled to −78° C. (acetone/dry ice), and LDA (13 mL, 26 mmol) was added dropwise. Reaction mixture was stirred at this temperature for 1 h. In a separate flask 6-(4'-iodobutoxy)-2,2-dimethylhexanoate (3.62 g, 10.0 mmol) was dissolved in THF (25 ml) and cooled to −78° C. To this solution of dilithium isobutyrate was transferred (cannula) under N2 slowly (1 h) with stirring, and the reaction mixture was stirred for 1 h at −78° C. After 12 h reaction mixture was allowed to reach −5° C. The cold solution was quenched with a mixture of ice/water and HCl (25 mL, pH=4), and ethyl ether (20 mL) was added. Layers were separated, and water layer was extracted with ethyl ether (30 mL). Combined organic layer were dried over $Na_2SO_4$. Solvent was removed by rotary evaporation and the residue was dried under vacuum (oil pump) to give crude (unstable during distillation), 6-(6-ethoxy-5,5-dimethyl-6-oxohexanoxy)-2,2-dimethylhexanoic acid (3.40 g) as an oil.

Crude 6-(6-ethoxy-5,5-dimethyl-6-oxohexanoxy)-2,2-dimethylhexanoic acid (1.24 g) was dissolved in $CH_2Cl_2$ (15 mL) and the mixture was cooled to 0° C. Oxalyl chloride (2 M solution in $CH_2Cl_2$; 9.0 mL, 18 mmol) was slowly added with stirring under $N_2$. After 30 min. at RT an additional amount of oxalyl chloride (9.0 mL, 18.0 mmol) was added. The resulting solution was stirred for 2 h and concentrated under reduced pressure (25° C./10 mmHg) to give 6-(6-ethoxy-5,5-dimethyl-6-oxohexanoxy)-2,2-dimethylhexanoyl chloride as an oil (1.12 g, 3.21 mmol, 60%).

IR ($CH_2Cl_2$) 2979, 2945, 2867, 1782, 1718, 1472, 1369, 1112, 905 $cm^{-1}$.

NMR: $^1H$ (200 MHz, $CDCl_3$) 4.11 (q, J=7.1, 2H, $OCH_2CH_2$), 3.43 (t, J=6.4, 2H, $CH_2O$), 3.38 (t, J=6.51, 2H, $CH_2O$), 1.68-1.46 (m, 8H, $2CCH_2CH_2C$), 1.39-1.12 (m, 19H, 2 $CH_2(CH_3)_2$, $CH_3$).

e. 6-(6-Ethoxy-5,5-dimethyl-6-oxohexanoxy)-2,2-dimethylhexanoyl-L-carnitine benzyl ester chloride/bromide/iodide A flask was charged with L-carnitine benzyl ester bromide (1.000 g, 3.012 mmol), 6-(6-ethoxy-5,5-dimethyl-6-oxohexanoxy)-2,2-dimethylhexanoic acid chloride (0.8713 g, 2.500 mmol), and acetonitrile (12 mL). The mixture was refluxed under $N_2$ and L-carnitine benzyl ester bromide gradually dissolved in acetonitrile. After 18 h, solvent was removed under reduced pressure. The oily residue was washed with ethyl ether (2×5 mL) and the residue was dissolved in $CHCl_3$ (5 mL), and ethyl ether (5 mL) was added to form a precipitate. The mixture was kept in freezer (−15° C.) for 12 h and solid of unreacted 1-carnitine ester bromide (0.171 g) was filtered off. Solvents were removed under reduced pressure to give 6-(6' ethoxy-5,5-dimethyl-6-oxohexanoxy)-2,2-dimethylhexanoyl-L-carnitine benzyl ester chloride/bromide/iodide as an oil. Oil was dried on vacuum (oil pump) to give crude (that contained also L-carnitine benzyl ester chloride/bromide/iodide) (foam) (1.379 g).

IR ($CH_2Cl_2$) 3440, 2944, 1730, 1478, 1322, 1183, 1139 $cm^{-1}$.

NMR: $^1H$ (200 MHz, $D_2O$) 7.48-7.36 (m, 5H, $C_6H_5$), 5.76-5.61 (m, 1H, CH), 5.19 (d, J=3.1, 2H, $CH_2C_6H_5$), 4.16 (q, J=7.1, 2H, $CH_2CH_3$), 4.04-3.66 (m, 2H, $CH_2N$), 3.51-3.39 (m, 4H, 2 $CH_2O$), 3.17 (s, 9H, $N(CH_3)_3$), 2.88-2.81 (m, 2H, $CH_2COO$), 1.63-1.43 (m, $2CCH_2CH_2C$), 1.41-1.11 (m, 19H, $2CH(CH_3)_2$, $CH_2CH_3$).

MS (FAB, gly) (positive) 706 (7%), 564 (100%, $M^+$).

f. 6-(6-Ethoxy-5,5-dimethyl-6-oxohexanoxy)-2,2-dimethylhexanoyl-L-carnitine hydrochloride/bromide A flask was charged with 6-(6-ethoxy-5,5-dimethyl-6-oxohexanoxy)-2,2-dimethylhexanoyl-L-carnitine benzyl ester chloride/bromide/iodide (0.2998 g, 0.500 mmol), THF (10 mL) under $N_2$, and immersed in water bath at 25° C. Palladium/carbon (10%, 0.2998 g) was added and excess of $H_2$ (>11.2 mL, 5.0 mmol) was delivered in a rubber balloon. The reaction was stirred for a minimum of 2 h and the mixture was filtered (celite) and washed with hot THF (5 mL). Solvent was removed from the combined filtrates by rotary evaporation to give crude 6-(6-ethoxy-5,5-dimethyl-6-oxohexanoxy)-2,2-dimethylhexanoyl-L-carnitine hydrochloride/bromide/iodide as a white solid (0.2292 g, 0.45 mmol, 90%), m.p. 148-151° C. (hygroscopic).

g. Purification of 6-(6-ethoxy-5,5-dimethyl-6-oxohexanoxy)-2,2-dimethylhexanoyl-L-carnitine hydrochloride/bromide Via Reaction with Silica Gel Functionalized Propionyl Chloride Crude 6-(6-ethoxy-5,5-dimethyl-6-oxohexanoxy)-2,2-dimethylhexanoyl-L-carnitine hydrochloride/bromide/iodide (0.300 g, 0.522 mmol), silica gel/propionyl chloride (0.0522 g), and acetonitrile (8 mL) were refluxed for 6 h. Silica gel was filtered off and washed with hot (50° C.) acetonitrile (5 mL). Solvent was removed from combined filtrates by rotary evaporation and the residue was dried by oil pump vacuum to give the purified product as chloride/bromide/iodide foam (0.2430 g, 81%), m.p. 149-151° C. (hygroscopic).

IR (KBr) 2982, 2946, 2869, 1740, 1724, 1475, 1391, 1135 cm$^{-1}$.

NMR: $^1$H (200 Mz, D$_2$O) 5.78-5.63 (m, 1H CH), 4.20 (q, J=7.1, 2H, CH$_2$CH$_3$), 4.07-3.69 (m, 2H, CH$_2$N), 3.49 (t, J=6.3, 4H, 2CH$_2$O), 3.22 (s, 9H, N(CH$_3$)$_3$), 2.93-2.82 (m, 2H, CH$_2$COO), 1.66-1.44 (m, 8H, 2CCH$_2$CH$_2$C), 1.29-1.02 (m, 19H, 2CH(CH$_3$)$_2$, CH$_2$CH$_3$); $^1$H (200 M DMSO-d$_6$) 5.52-5.38 (m, 1H, CH), 4.06 (q, J=6.3, 21H, CH$_2$CH$_3$), 3.97-3.35 (m, 2H$_1$CH$_2$N), 3.29 (t, J=6.3, 4H, 2CH$_2$O), 3.16 (9H, N(CH$_3$)$_3$), 2.84-2.71 (m, 2H, CH$_2$COO), 1.58-1.31 (m, 8H, 2CCH$_2$CH$_2$C), 1.31-0.97 (m, 19H, 2CH(CH$_3$)$_2$, CH$_2$CH$_3$); $^{13}$C (50 MHz, D$_2$O and acetonitrile as internal reference) 179.6, 171.6, (missing CO), 70.7, 68.6, 65.9, 63.0, 54.3, 42.8, 39.9, 38.1, 29.7, 24.8, 24.3, 21.5, 13.9, $^{13}$C (DMSO-d$_6$) 175.9, 168.869.7, 67.0, 64.9, 60.6, 59.7, 52.8, 29.6, 25.5, 24.8, 21.0, 14.0.

MS (FAB, gly) (positive) 502 (12%), 474 (100%, M$^+$), 446 (18%), 360 (22%). Calc. for C$_{25}$H$_{48}$BrNO$_7$: C, 54.15; H, 8.72. Found: C, 49.62; H, 8.13. Calc. for C$_2$H$_{48}$INO$_7$: C, 49.92; H, 8.04. Found: C, 49.62; H, 8.13.

EXAMPLE 3 a. 6,6'-Oxybis(2,2-dimethylhexanoic) acid

To a solution of isobutyric acid (IBA) (3.70 g, 42.0 mmol) in anhydrous THF (20 mL), LDA (2.0 M in THF/hexanes; 42 mL, 84 mmol) was added dropwise at −30° C. under N$_2$ atmosphere. Next, 4-chlorobutyl ether (3.98 g, 20.0 mmol) was added dropwise. Reaction mixture was allowed to warm to RT with stirring, change of color to yellow was observed at −10° C. After 2 h the mixture was refluxed for 30 min, and cooled to RT. The cold solution was quenched with water (30 mL). Layers were separated. Aqueous layer (pH=12) was extracted with ether (3×20 mL) and next acidified with diluted HCl to pH=2. Aqueous layer was extracted with ether (3×20 mL). Combined last three (after acidification) ether extracts were dried over Na$_2$SO$_4$ and the solvent was removed by rotary evaporation. Column chromatography (silica gel, hexane/ethyl acetate, 4:1 v/v) gave 6,6'-oxybis(2,2-dimethylhexanoic) acid as a white solid (3.44 g, 11.4 mmol, 57%), m.p. 49-51° C.

R$_f$=0.50 (silica gel, hexane/ethyl acetate, 4:1 v/v).

IR (KBr) 2863, 1703, 1475, 1405, 1286, 1204, 1120 cm$^{-1}$.

NMR: $^1$H (200 MHz, CDCl$_3$) 10.85 (s, br, 2H, COOH), 3.38 (t, J=5.5, 4H, 2CH$_2$O), 1.60-1.49 (m, 8H, 2CCH$_2$CH$_2$C), 1.47-1.30 (m, 4H, 2CH$_2$C(CH$_3$)$_2$), 1.20 (s, 12H, 4 CH$_3$); $^{13}$C (50 MHz, CDCl$_3$) 184.9, 70.2, 42.6, 41.5, 30.3, 25.0, 22.2.

MS (FAB, methanol) (negative) 301 (100%, (M−1)$^-$.

b. 6,6'-Oxybis(2,2-dimethylhexanoyl chloride), (9) Scheme 2, R$^1$, R$^2$ are —CH$_3$ A flask was charged with 6,6'-oxybis(2,2-diethylhexanoic) acid (0.604 g, 2.00 mmol) and CH$_2$Cl$_2$ (3 ml), and the mixture was cooled to 0° C. Oxalyl chloride (2.0 M in CH$_2$Cl$_2$; 3.0 mL, 6.00 mmol) was slowly added with stirring under N$_2$. After stirring at RT for 30 min, further amount of oxalyl chloride (4.0 mL, 8.0 mmol) was added. The solution was stirred for 2 h and concentrated by rotary evaporation. 6,6'-Oxybis(2,2-dimethylhexanoyl chloride) was obtained as colorless oil (0.61 g, 1.8 mmol, 90%).

IR (CH$_2$Cl$_2$) 2947, 2876, 1782, 1470, 1112, 904 cm$^{-1}$.

NMR: $^1$H (200 MHz, CDCl$_3$) 3.41 (t, J=6.3, 4H, 2CH$_2$O), 1.73-1.49 (m, 8H, 2CCH$_2$CH$_2$C), 1.44-1.25 (m, 16H, 2 CH$_2$C (CH$_3$)$_2$, 4 CH$_3$); $^{13}$C (50 MHz, CDCl$_3$) 180.5, 70.7, 53.2, 40.5, 30.3, 25.5, 21.8.

c. 6,6'-Oxybis(2,2-dimethylhexanoyl-L-carnitine benzyl ester chloride), (10) Scheme 2

A flask was charged with 6,6'-oxybis(2,2-dimethylhexanoyl chloride) (0.6778 g, 2.000 mmol), L-carnitine benzyl ester bromide (1.66 g, 5.00 mmol), and acetonitrile (13 mL). Reaction mixture was stirred at 65° C. under N$_2$. Suspension of L-carnitine benzyl ester bromide gradually dissolved. After 15 h, solvent was removed by rotary evaporation. Oily residue was dissolved in acetone (5 mL) and ether (5 mL) was added. The mixture was kept in the freezer (−15° C.) for 5 h, and solid was filtered off. Solvent was removed from filtrate by rotary evaporation to give 6,6'-Oxybis(2,2-dimethylhexanoyl-L-carnitine benzyl ester chloride) as an oil (1.778 g).

R$_f$=0.57 (chloroform/methanol, 4:1 v/v).

d. Purification of 6,6'-oxybis(2,2-dimethylhexanoyl-L-carnitine benzyl ester chloride/bromide) Via Reaction with Silica Gel Functionalized Propionyl Chloride Crude of 6,6'-oxybis(2,2-dimethylhexanoyl-L-carnitine benzyl ester chloride/bromide) (0.3000 g, 03224 mmol), silica gel/propionyl chloride (0.03 g), and acetonitrile (8 mL) were refluxed for 6 h. Silica gel was filtered off and washed with hot acetonitrile (5 mL). Solvent was removed from combined filtrates by rotary evaporation and the residue was dried by oil pump vacuum to give product chloride/bromide as a foam (0.2810 g, 94%).

IR (KBr) 3433, 2945, 2867, 1734, 1475, 1180, 1135 cm$^{-1}$.

NMR: $^1$H (200 MHz, D$_2$O) 7.48-7.27 (s, 10$_{aromat}$), 5.71-5.57 (m, 2H, CH), 5.16 (d, J=2.7, 4H, 2OCH$_2$benzyl), 4.0-3.56 (m, 4H, 2NCH$_2$), 3.33 (t, J=6.4, 4H, 2OCH$_2$) 3.13 (s, 18H, 2 N(CH$_3$)$_3$), 2.95-2.71 (m, 4H, 2 CH$_2$COO), 1.56-1.32 (m, 8H, 2 CCH$_2$CH$_2$C), 1.30-0.97 (m, 16H, 2 CH$_2$C(CH$_3$)$_2$); $^{13}$C (50 MHz, D$_2$O and acetonitrile as internal reference) 179.5, 171.2 135.7, 129.5, 129.2 (ipso signal 129.6 127.0 see spectra L-carnitine benzyl ester bromide), 70.7, 68.6, 68.2, 65.8, 54.4, 42.7, 40.0, 38.2, 29.7, 24.8, 24.3, 21.6.

e. 6,6'-oxybis(2,2-dimethylhexanoyl-L-carnitine hydrochloride/bromide)

A flask was charged with 6,6'-oxybis(2,2-dimethylhexanoyl-L-carnitine benzyl ester chloride/bromide) (0.4205 g, 0.500 mmol), THF (15 mL) under N$_2$, and immersed in a water bath at 25° C. Palladium/carbon (10%, 0.8410 g) was added and excess of H$_2$ (22.4 mL, 10.0 mmol) was delivered in a rubber balloon. The reaction was stirred for 12 h and the mixture was filtered (celite) and washed with hot THF (10 mL). Solvent was removed from the combined filtrates by rotary evaporation to give 6,6'-oxybis(2,2-dimethylhexanoyl-L-carnitine hydrochloride/bromide) as a white (hygroscopic) solid (foam) (0.298 g, 0.450 mmol, 90%).

IR (KBr) 2943, 2869, 1728, 1476, 1391, 1181, 1138 cm$^{-1}$.

NMR: $^1$H (200 MHz, D$_2$O) 5.73-5.57 (m, 2H, 2CH), 4.07-3.64 (m, 4H, 2CH$_2$N), 3.46 (t, J=6.2, 4H, 2CH$_2$O), 3.19 (s, 18H, 2 N(CH$_3$)$_3$), 2.83 (d, J=6.0, 4H, 2CH$_2$COO), 1.66-1.41

(m, 8H, 2CCH$_2$CH$_2$C), 1.39-1.08 (m, 16H, 2CH$_2$C(CH$_3$)$_2$); $^1$H (200 MHz, DMSO-d$_6$) 12.52 (s, broad, 2COOH), 5.50-5.34 (m, 2H, 2CH), 3.97-3.63 (m, 4H, 2CH$_2$N), 3.30 (t, J=6.1, 4H, 2CH$_2$O), 3.12 (s, 18H, 2N(CH$_3$)$_3$), 2.67 (d, J=4.3, 4H, 2CH$_2$COO), 1.57-1.30 (m, 8H, 2CCH$_2$CH$_2$C), 1.30-1.04 (m, 16H, 2CH$_2$C(CH$_3$)$_2$); $^{13}$C (D$_2$O and acetonitrile as an internal reference) 179.7, 173.4, 70.3, 68.6, 65.9, 54.4, 42.8, 40.0, 37.8, 29.6, 24.9, 24.2, 21.6.

MS (FAB, gly) (positive) 672 (27%), 588 (22%, M$^+$), 530 (33%), 508 (15%), 464 (52%), 446 (100%), no other peaks >40% above 400.

EXAMPLE 4 a. 15-Ethoxycarbonyl-3,3,14,14-tatramethylpentadecanoic acid, (46) in Scheme 7

The precursor 1,1,14,14-tetra(ethoxycarbonyl)-2,2,13,13-tetramethyldecane (43 in Scheme 7) was synthesized according to the published procedure by Bar-Tana, J., in U.S. Pat. No. 4,689,344. A solution of (43) (18.46 g, 0.034 mol) and potassium hydroxide (85%, 15.23 g, 0.232 mol) in EtOH (100 mL) was heated to reflux for 18.5 h. The solvent was evaporated and the residue dissolved in water (100 mL). The mixture was extracted with MTBE (100 mL). The aqueous layer was acidified with conc. HCl (15 mL) and extracted with diethyl ether (150 mL). The solution was dried over MgSO$_4$, filtered, and concentrated under reduced pressure to yield the corresponding tetracarboxylic acid (18.14 g). This material was heated to 190° C. for 1 h. Thionyl chloride (20 mL) and DMF (1 drop) was added to the formed dicarboxylic acid (44), and the reaction mixture was heated to reflux for 2.5 h. The excess thionyl chloride was distilled off. The residue was dissolved in toluene (20 mL), concentrated under reduced pressure, and then redissolved in dichloromethane (20 mL). This dichloromethane solution was then added dropwise to ethanol (30 mL) at −78° C. After evaporation of the solvent, 1,14-diethoxycarbonyl-2,2,13,13-tetramethyltetradecane (45, 11.1 g) was obtained as a dark oil. A solution of (45, (11.1 g, 27.8 mmol) and KOH (85%, 1.56 g, 23.7 mmol) in ethanol (20 mL) was heated to reflux for 15 h and evaporated. The residue was dissolved in diethyl ether (50 mL) and the formed solution was treated under ice cooling with conc. HCl (5 mL). The organic layer was separated, dried over MgSO$_4$ and evaporated. The residue was purified by column chromatography (silica gel, EtOAc-heptane, 1:4) to give 15-ethoxycarbonyl-3,3,14,14-tetramethylpentadecanoic acid (46, 2.88 g, 23%) as an oil.

$^1$H NMR (300 MHz, CDCl$_3$/TMS): δ 4.13 (q, J=7.1H, 2H), 2.23 (s, 2H), 2.18 (s, 2H), 1.26 (m, 23H), 1.02 (s, 6H), 0.98 (s, 6H).

$^{13}$C NMR (75 MHz, CDCl$_3$/TMS): δ 178.85, 172.62, 60.10, 46.37, 46.16, 42.68, 42.64, 33.56, 33.48, 30.67, 29.94, 27.62, 27.51, 24.36, 14.64.

b. 15-Ethoxycarbonyl-3,3,14,14-tetramethylpentadecanoyl-L-carnitine (47)

To a solution of 15-ethoxycarbonyl-3,3,14,14-tatramethylpentadecanoic acid (46) (1.31 g, 3.53 mmol) in SOCl$_2$ (5 mL) was added DMF (one drop) and the mixture was heated to 60° C. for 2 h. Toluene (10 mL) was added and the solvents were evaporated. The residue was dried in vacuum (1 mm Hg) for 1 h and treated with solution of L-carnitine (0.57 g, 3.53 mmol) in TFA (3.0 mL) at RT (22° C.). The mixture was kept at RT overnight and was then heated to 55° C. for 3 h. The reaction mixture was concentrated and the residue was dissolved in CH$_2$Cl$_2$ (50 mL). The solution was washed with water (10 mL), dried over molecular sieves (4 Å) in the presence of charcoal, and evaporated. The residue was washed with heptane (2×10 mL), concentrated, and dried in vacuum. Purification by column chromatography (reverse-phase C$_{18}$-silica gel, EtOH—H$_2$O, 3:1), dissolution in dichloromethane, drying over molecular sieves (4 Å), and concentration in vacuo afforded 15-ethoxycarbonyl-3,3,14,14-tetramethylpentadecanoyol-carnitine (0.82 g, 41%) as a colorless, sticky oil.

$^1$H NMR (300 MHz, CD$_3$OD/TMS)-5.60 (m, 1H), 4.09 (q, J=7.1 Hz, 2H), 3.86 (dd, J=14.0, 8.2 Hz, 1H), 3.70 (d, J=14.0 Hz, 1H), 3.19 (s, 9H), 2.76 (m, 2H), 2.29 (AB, J=14.0 Hz, 2H), 2.18 (s, 2H), 1.29 (m, 23H), 1.01 (s, 6H), 0.98 (s, 6H).

$^{13}$C NMR (75, CD$_3$OD): 173.86, 172.38, 172.24, 69.48, 66.09, 61.05, 54.49, 46.82, 46.49, 43.39, 37.96, 34.28, 34.17, 31.56, 30.78, 27.94, 27.71, 25.15, 14.72.

HRMS (LSIMS, nba): Calc. For C$_{29}$H$_{56}$O$_6$N (MH$^+$): 514.4108, found: 514.4082.

HPLC (Synergi Polar-RP, 4μ, 4.6×250 mm, 1.0 mL/min, RI detection; 60% acetonitrile, 40% aqueous KH$_2$PO$_4$ (0.025 m, pH 3); retention time 7.98 min): 88.0% pure.

Elemental analysis for assumed hydrochloride salt (C$_{29}$H$_{56}$O$_6$NCl): calc. C, 63.31; H, 10.26; N, 2.55; Cl, 6.44. Found: C, 54.70; H, 8.60; N, 2.13; Cl, 0.41.

Assignment of NMR Resonances to Specific Protons/Carbons:

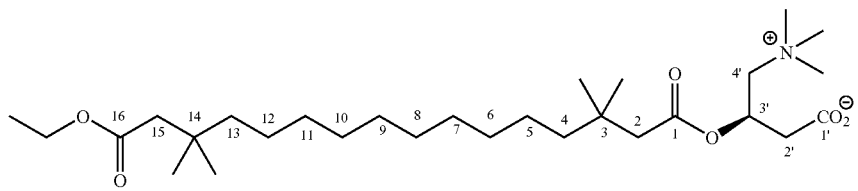

| $^1$H resonance [ppm] | Assignment | $^{13}$C resonance [ppm] | Assignment |
|---|---|---|---|
| 5.60 (m, 1 H) | H-3' | 173.86 | C-1', C-1, or C-16 |
| 4.09 (q, J = 7.1 MHz, 2 H) | Ethyl-CH$_2$ | 172.38 | C-1', C-1, or C-16 |
| 3.86 (dd, J = 14.0, 8.2 Hz, 1 H) | H-4' | 172.24 | C-1', C-1, or C-16 |
| 3.70 (d, J = 14.0 Hz, 1 H) | H-4' | 69.48 | C-4' |
| 3.19 (s, 9 H) | N$^+$(CH$_3$)$_3$ | 66.09 | C-3' |
| 2.76 (m, 2 H) | H-2' | 61.05 | CH$_3$—CH$_2$ |
| 2.29 (AB, J = 14.0 Hz, 2 H) | H-2 | 54.49 | N$^+$(CH$_3$)$_3$ |

-continued

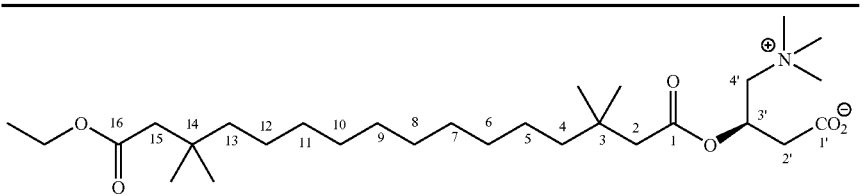

| $^1$H resonance [ppm] | Assignment | $^{13}$C resonance [ppm] | Assignment |
| --- | --- | --- | --- |
| 2.18 (s, 2 H) | H-15 | 46.82 | C-2 or C-15 |
| 1.29 (m, 23 H) | H-4 to H-13, ethyl-CH$_3$ | 46.49 | C-2 or C-15 |
| 1.01 (s, 6 H) | C—CH$_3$ | 43.39 | C-4 or C-13 |
| 0.98 (s, 6 H) | C—CH$_3$ | 37.96 | C-4 or C-13 |
| | | 34.28 | Alkyl-, |
| | | 34.17 | methyl-carbons |
| | | 31.56 | |
| | | 30.78 | |
| | | 27.94 | |
| | | 27.71 | |
| | | 25.15 | |
| | | 14.72 | CH$_3$—CH$_2$ |

Other embodiments of the invention will be apparent to those skilled in the art from a consideration of this specification or practice of the invention disclosed herein. It is intended that the specification and examples be considered as exemplarily only, with the true scope and spirit of the invention being indicated by the following claims.

What is claimed is:

1. A process for the preparation of intermediate compounds, wherein such intermediate compound has the Formula

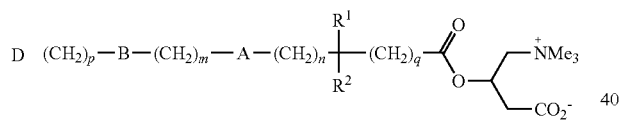

wherein A is —O—; m is 4; n is 4; p is 0; q is 0; B is —CR$^1$R$^2$; D is —COOR$^5$;

R$^1$ and R$^2$ are independently selected from the group consisting of hydrogen; C$_1$-C$_6$-alkyl; C$_3$-C$_6$ cycloalkyl; C$_2$-C$_6$ alkenyl; C$_6$ alkynyl; C$_5$-C$_{10}$ aryl unsubstituted or substituted with C$_1$-C$_6$ alkyl, hydroxyl, C$_1$-C$_6$ alkoxyl, 1,3-dioxolanyl, cyano, halo, nitro, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, C$_1$-C$_6$ acylamino, mercapto, C$_1$-C$_6$ alkylthio, C$_1$-C$_6$ mercaptoalkyl, and C$_1$-C$_6$ alkoxycarbonyl; and C$_5$-C$_6$ arylalkyl unsubstituted or substituted with C$_1$-C$_6$ alkyl, hydroxyl, C$_1$-C$_6$ alkoxyl, 1,3-dioxolanyl, cyano, halo, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, mercapto, C$_1$-C$_6$ alkylthio, C$_1$-C$_6$ mercaptoalkyl, and C$_1$-C$_6$ alkoxycarbonyl; C$_1$-C$_6$ carboxyalkyl; C$_1$-C$_6$ acylamino; C$_1$-C$_6$ sulfonatoalkyl; C$_1$-C$_6$ sulfamylalkyl; and C$_1$-C$_6$ phosphonatoalkyl;

R$^1$ and R$^2$ may optionally be tethered together to form a 3- to 7-membered alicyclic ring; and R$^5$ is independently selected from the group consisting of hydrogen; C$_1$-C$_6$ alkyl; and C$_5$-C$_6$ arylalkyl unsubstituted or substituted with C$_1$-C$_6$ alkyl; which comprises the following steps:

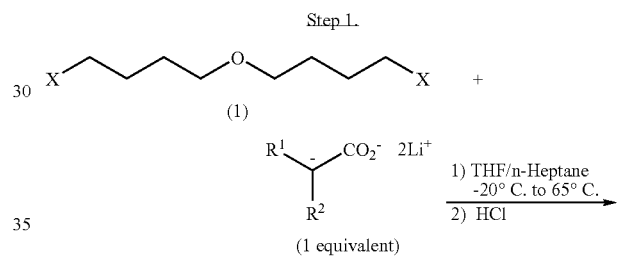

where X=halogen or a leaving group; and R$^1$ and R$^2$ are defined as above; and

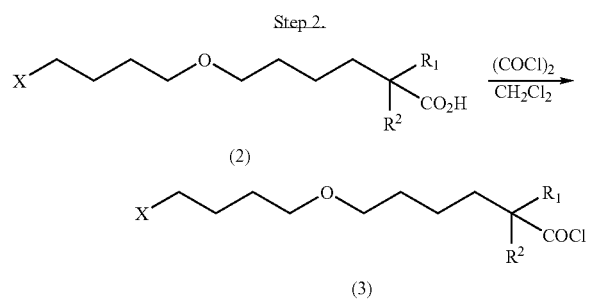

where R$^1$ and R$^2$ are defined as above; and

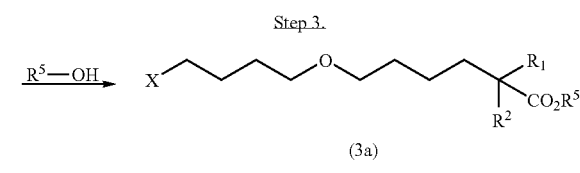

where R$^1$, R$^2$ and R$^5$ are defined as above, and

Step 4.

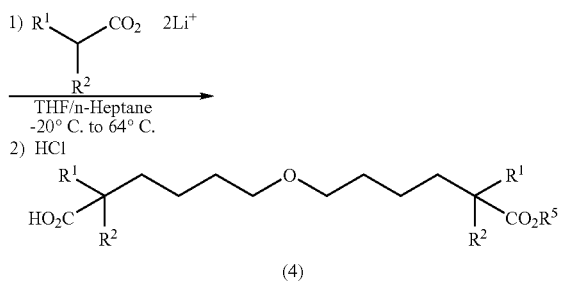

(4)

where $R^1$, and $R^2$ and $R^5$ are defined as above is Et; and

Step 5.

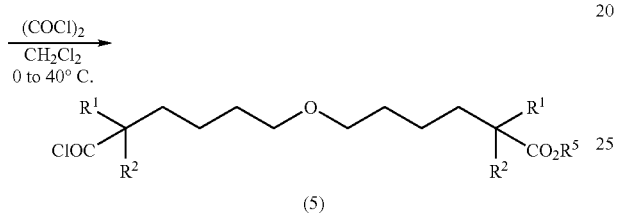

(5)

where $R^1$, $R^2$ and $R^5$ are defined as above; and

Step 6.

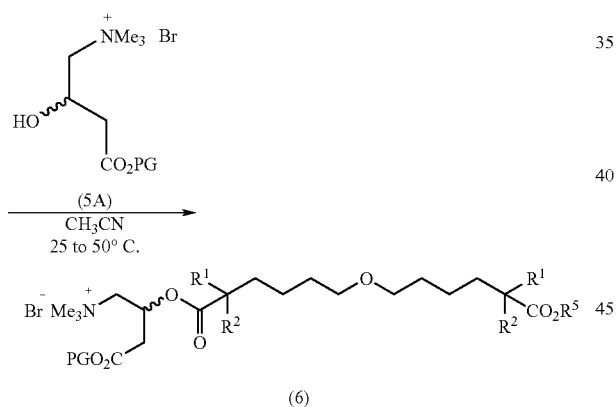

(6)

wherein PG is a protecting group chosen to be hydrogen, t-butyl, or a substituted or unsubstituted benzyl group of the formula

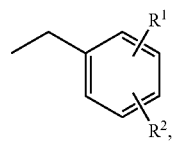

wherein $R^1$, $R^2$ and $R^5$ are as defined as above, and carnitine with a protecting group PG(5A) in Step 6 may be of D, L, or DL configuration; and Step 7.
when PG is

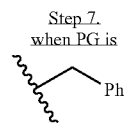

1) 10-20% Pd/C, $H_2$
   THF/$CH_3OH$
2) adjust pH
3) RP chromatography

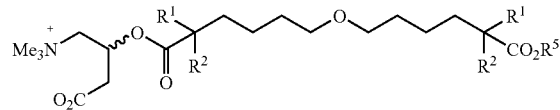

(7)

where $R^1$ and $R^2$ are defined as above, and $R^5$ is $C_1$-$C_6$ alkyl; or when $R^5$ is

then Step 7 above yields

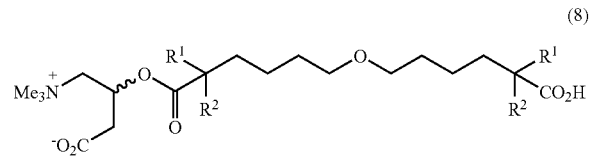

(8)

where $R^1$ and $R^2$ are defined as above, and $R^5$ is hydrogen.

* * * * *